US011129823B2

(12) United States Patent
Brady et al.

(10) Patent No.: US 11,129,823 B2
(45) Date of Patent: Sep. 28, 2021

(54) COMBINATION TREATMENT OF OCULAR INFLAMMATORY DISORDERS AND DISEASES

(71) Applicant: Aldeyra Therapeutics, Inc., Lexington, MA (US)

(72) Inventors: Todd Brady, Lexington, MA (US); Scott Young, E. Falmouth, MA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 0 days.

(21) Appl. No.: 16/300,020

(22) PCT Filed: May 9, 2017

(86) PCT No.: PCT/US2017/031808
§ 371 (c)(1),
(2) Date: Nov. 8, 2018

(87) PCT Pub. No.: WO2017/196881
PCT Pub. Date: Nov. 16, 2017

(65) Prior Publication Data
US 2019/0183878 A1 Jun. 20, 2019

Related U.S. Application Data

(60) Provisional application No. 62/333,549, filed on May 9, 2016.

(51) Int. Cl.
| | | |
|---|---|---|
| *A61K 31/47* | (2006.01) | |
| *A61K 47/40* | (2006.01) | |
| *A61K 45/06* | (2006.01) | |
| *A61K 9/00* | (2006.01) | |
| *A61P 27/02* | (2006.01) | |
| *A61P 29/00* | (2006.01) | |
| *A61K 31/192* | (2006.01) | |
| *A61K 31/196* | (2006.01) | |
| *A61K 31/573* | (2006.01) | |
| *A61K 31/165* | (2006.01) | |
| *A61K 31/436* | (2006.01) | |
| *A61K 9/08* | (2006.01) | |
| *A61K 31/519* | (2006.01) | |

(52) U.S. Cl.
CPC ............ *A61K 31/47* (2013.01); *A61K 9/0048* (2013.01); *A61K 9/08* (2013.01); *A61K 31/165* (2013.01); *A61K 31/192* (2013.01); *A61K 31/196* (2013.01); *A61K 31/436* (2013.01); *A61K 31/519* (2013.01); *A61K 31/573* (2013.01); *A61K 45/06* (2013.01); *A61K 47/40* (2013.01); *A61P 27/02* (2018.01); *A61P 29/00* (2018.01)

(58) Field of Classification Search
CPC ........ A61K 31/47; A61K 9/0048; A61K 9/08; A61K 31/165; A61K 31/192; A61K 31/196; A61K 31/436; A61K 31/519; A61K 31/573; A61K 45/06; A61K 47/40; A61P 27/02; A61P 29/00
See application file for complete search history.

(56) References Cited

U.S. PATENT DOCUMENTS

| | | |
|---|---|---|
| 2,086,186 A | 7/1937 | Messer |
| 3,912,748 A | 10/1975 | Evans et al. |
| 4,668,626 A | 5/1987 | Kobayashi et al. |
| 4,956,351 A | 9/1990 | Mesens et al. |
| 5,024,998 A | 6/1991 | Bodor |
| 5,364,637 A | 11/1994 | De et al. |
| 5,376,645 A | 12/1994 | Stella et al. |
| 5,419,898 A | 5/1995 | Ikejiri et al. |
| 5,472,954 A | 12/1995 | Loftsson |
| 5,493,027 A | 2/1996 | Nichols et al. |
| 5,576,311 A | 11/1996 | Guy |
| 5,668,117 A | 9/1997 | Shapiro |
| 5,767,109 A | 6/1998 | Sanchez et al. |
| 5,998,488 A | 12/1999 | Shinohara et al. |
| 6,191,127 B1 | 2/2001 | Holscher et al. |
| 6,358,948 B1 | 3/2002 | Zhang et al. |
| 6,444,221 B1 | 9/2002 | Shapiro |
| 6,498,154 B1 | 12/2002 | Grubb et al. |
| 6,515,010 B1 | 2/2003 | Franchini et al. |
| 6,569,879 B2 | 5/2003 | Liu |
| 7,083,803 B2 | 8/2006 | Peyman |
| 7,297,709 B2 | 11/2007 | Dai et al. |
| 7,531,564 B2 | 5/2009 | Malamas et al. |

(Continued)

FOREIGN PATENT DOCUMENTS

| | | |
|---|---|---|
| CN | 1882339 A | 12/2006 |
| CN | 101048384 A | 10/2007 |

(Continued)

OTHER PUBLICATIONS

Abelson et al., "Conjunctival allergen challenge. A clinical approach to studying allergic conjunctivitis," Archives of Ophthalmology, 108(1):84-88 (1990).
Abelson et al., "Combined analysis of two studies using the conjunctival allergen challenge model to evaluate olopatadine hydrochloride, a new ophthalmic antiallergic agent with dual activity," American Journal of Ophthalmology, 125(6):797-804 (1998).
Abelson et al., "Conjunctival allergen challenge: models in the investigation of ocular allergy," Current Allergy and Asthma Reports, 3(4):363-368 (2003).
Abramovitz, M. et al., "The utilization of recombinant prostanoid receptors to determine the affinities and selectivities of prostaglandins and related analogs," Biochem. Biophys. Acta., 1483(2):285-293 (2000).

(Continued)

*Primary Examiner* — Kortney L. Klinkel
*Assistant Examiner* — William Y Lee
(74) *Attorney, Agent, or Firm* — Dechert LLP; Andrea L. C. Reid; Joseph W. Arico

(57) ABSTRACT

The present disclosure provides a combination of a fused bicyclic amine compound and an anti-inflammatory agent for treating ocular inflammatory disorders and diseases. Further provided are pharmaceutical compositions of the compound and the anti-inflammatory agent.

4 Claims, 3 Drawing Sheets

(56) References Cited

U.S. PATENT DOCUMENTS

| | | |
|---|---|---|
| 7,973,025 B2 | 7/2011 | Jordan et al. |
| 7,982,071 B2 | 7/2011 | Scott et al. |
| 8,158,609 B1 | 4/2012 | Marsh et al. |
| 8,435,965 B2 | 5/2013 | Tabuchi et al. |
| 8,575,221 B2 | 11/2013 | Masse et al. |
| 8,722,669 B2 | 5/2014 | Palczewski et al. |
| 8,791,154 B2 | 7/2014 | Gamache et al. |
| 8,940,721 B2 | 1/2015 | Jordan et al. |
| 8,940,764 B2 | 1/2015 | Jordan et al. |
| 9,067,963 B2 | 6/2015 | Thompson et al. |
| 9,265,759 B2 | 2/2016 | Jordan et al. |
| 9,364,471 B2 | 6/2016 | Jordan et al. |
| 9,375,408 B2 | 6/2016 | Singh |
| 9,604,997 B2 | 3/2017 | Jordan |
| 9,650,342 B2 | 5/2017 | Jordan et al. |
| 9,687,481 B2 | 6/2017 | Brady et al. |
| 9,814,701 B2 | 11/2017 | Jordan et al. |
| 9,896,419 B2 | 2/2018 | Jordan et al. |
| 10,058,095 B2 | 8/2018 | Czarnik |
| 10,111,862 B2 | 10/2018 | Chabala et al. |
| 10,202,348 B2 | 2/2019 | Jordan et al. |
| 10,213,395 B2 | 2/2019 | Brady et al. |
| 10,414,732 B2 | 9/2019 | Buist et al. |
| 10,426,790 B2 | 10/2019 | Young et al. |
| 10,543,181 B2 | 1/2020 | Brady et al. |
| 10,550,085 B2 | 2/2020 | Brady et al. |
| 10,588,874 B2 | 3/2020 | Brady et al. |
| 10,913,722 B2 | 2/2021 | Jordan et al. |
| 2004/0132636 A1 | 7/2004 | Dooley |
| 2004/0198828 A1 | 10/2004 | Abelson et al. |
| 2004/0235892 A1 | 11/2004 | Dai et al. |
| 2005/0020603 A1 | 1/2005 | Dai |
| 2005/0090553 A1 | 4/2005 | Shapiro |
| 2005/0130906 A1 | 6/2005 | Matier et al. |
| 2005/0197292 A1 | 9/2005 | Smithson et al. |
| 2005/0234018 A1* | 10/2005 | Lyons .................. A61K 9/0014 514/58 |
| 2006/0014786 A1 | 1/2006 | Raut |
| 2006/0111318 A1 | 5/2006 | Okamoto |
| 2006/0183909 A1 | 8/2006 | Schmitt et al. |
| 2006/0189608 A1 | 8/2006 | Bingaman |
| 2007/0129404 A1 | 6/2007 | Hagihara et al. |
| 2007/0135481 A1 | 6/2007 | Jordan et al. |
| 2009/0118503 A1 | 5/2009 | Sprott et al. |
| 2009/0182009 A1 | 7/2009 | Jordan et al. |
| 2010/0160304 A1 | 6/2010 | Katayama |
| 2010/0240624 A1 | 9/2010 | Chapin et al. |
| 2010/0331315 A1 | 12/2010 | Haddach et al. |
| 2011/0071091 A1 | 3/2011 | Chowhan et al. |
| 2011/0105450 A1 | 5/2011 | Chapin et al. |
| 2011/0263645 A1 | 10/2011 | Jordan et al. |
| 2012/0108585 A1 | 5/2012 | Vu |
| 2012/0295967 A1 | 11/2012 | Gamache et al. |
| 2012/0302601 A1 | 11/2012 | Jordan et al. |
| 2013/0165419 A1 | 6/2013 | Lindstrom et al. |
| 2013/0190500 A1 | 7/2013 | Greiner et al. |
| 2014/0038918 A1 | 2/2014 | Rodriguez-Boulan et al. |
| 2014/0235604 A1 | 8/2014 | Palczewski et al. |
| 2014/0235722 A1 | 8/2014 | Jordine et al. |
| 2015/0209333 A1 | 7/2015 | Jordan |
| 2015/0209345 A1 | 7/2015 | Jordan et al. |
| 2015/0258120 A1 | 9/2015 | Zarnitsyn et al. |
| 2015/0335632 A1 | 11/2015 | Brady et al. |
| 2015/0344432 A1 | 12/2015 | Jordan et al. |
| 2015/0344447 A1 | 12/2015 | Chabala et al. |
| 2016/0052930 A1 | 2/2016 | Fensome et al. |
| 2016/0168098 A1 | 6/2016 | Jordan et al. |
| 2017/0029354 A1 | 2/2017 | Singh |
| 2017/0143627 A1 | 5/2017 | Misra |
| 2017/0239196 A1 | 8/2017 | Brady et al. |
| 2017/0266220 A1 | 9/2017 | Young et al. |
| 2017/0320829 A1 | 11/2017 | Jordan et al. |
| 2018/0050989 A1 | 2/2018 | Machatha et al. |
| 2018/0092882 A1 | 4/2018 | Jordan et al. |
| 2018/0194733 A1 | 7/2018 | Jordan et al. |
| 2018/0235980 A1 | 8/2018 | Shah |
| 2018/0250306 A1 | 9/2018 | Brady et al. |
| 2018/0265474 A1 | 9/2018 | Buist et al. |
| 2018/0354905 A1 | 12/2018 | Brady et al. |
| 2019/0105322 A1 | 4/2019 | Macdonald et al. |
| 2019/0125729 A1 | 5/2019 | Chabala et al. |
| 2019/0210971 A1 | 7/2019 | Jordan et al. |
| 2019/0231715 A1 | 8/2019 | Brady et al. |
| 2020/0038392 A1 | 2/2020 | Brady et al. |
| 2020/0062712 A1 | 2/2020 | Machatha et al. |
| 2020/0121591 A1 | 4/2020 | Clark et al. |
| 2020/0199075 A1 | 6/2020 | Brady et al. |
| 2020/0246345 A1 | 8/2020 | Brady et al. |
| 2020/0323841 A1 | 10/2020 | Clark et al. |
| 2020/0368182 A1 | 11/2020 | Brady et al. |

FOREIGN PATENT DOCUMENTS

| | | |
|---|---|---|
| CN | 101321742 A | 12/2008 |
| CN | 101554826 A | 9/2009 |
| CN | 101611009 A | 12/2009 |
| EP | 0186367 A2 | 7/1986 |
| EP | 0245054 A1 | 11/1987 |
| EP | 0483881 A1 | 5/1992 |
| EP | 1621199 A1 | 1/2006 |
| EP | 1679308 A1 | 7/2006 |
| EP | 2301549 A1 | 3/2011 |
| EP | 1888548 B1 | 8/2012 |
| GB | 2327672 A | 2/1999 |
| JP | 2001041757 A | 6/2001 |
| JP | 2002003364 A | 1/2002 |
| JP | 3736916 B2 | 1/2006 |
| JP | 2007532648 A | 11/2007 |
| JP | 2008542291 A | 11/2008 |
| JP | 4466875 B2 | 5/2010 |
| JP | 4748289 B2 | 8/2011 |
| JP | 5194218 B2 | 5/2013 |
| JP | 2015-535293 A | 12/2015 |
| RU | 2010137842 A | 3/2012 |
| SU | 50906 A1 | 6/1984 |
| WO | WO 1996022992 A1 | 8/1996 |
| WO | WO 1998005645 | 2/1998 |
| WO | WO 1999046237 A1 | 9/1999 |
| WO | WO 2001041757 A1 | 6/2001 |
| WO | WO 2004082622 A2 | 9/2004 |
| WO | WO 2004091630 A1 | 10/2004 |
| WO | WO 2005035506 A1 | 4/2005 |
| WO | WO 2005040151 A1 | 5/2005 |
| WO | WO 2005051328 A2 | 6/2005 |
| WO | WO 2005079774 A2 | 9/2005 |
| WO | WO 2005105067 A2 | 11/2005 |
| WO | WO-2006000421 A2 | 1/2006 |
| WO | WO 2006002473 A1 | 1/2006 |
| WO | WO 2006049968 A1 | 5/2006 |
| WO | WO 2006077821 A1 | 7/2006 |
| WO | WO 2006127945 A1 | 11/2006 |
| WO | WO 2007118276 A1 | 10/2007 |
| WO | WO 2008014602 A1 | 2/2008 |
| WO | WO 2009045479 A1 | 4/2009 |
| WO | WO 2009102418 A1 | 8/2009 |
| WO | WO-2010048332 A2 | 4/2010 |
| WO | WO 2010133672 A1 | 11/2010 |
| WO | WO 2011008202 A1 | 1/2011 |
| WO | WO 2011071995 A2 | 6/2011 |
| WO | WO 2011072141 A1 | 6/2011 |
| WO | WO 2011078204 A1 | 6/2011 |
| WO | WO 2012097173 A2 | 7/2012 |
| WO | WO 2012105887 A1 | 8/2012 |
| WO | WO 2014100425 A1 | 6/2014 |
| WO | WO 2014116593 A1 | 7/2014 |
| WO | WO 2014116836 A2 | 7/2014 |
| WO | WO-2015002893 A1 | 1/2015 |
| WO | WO 2015187942 A1 | 12/2015 |
| WO | WO 2016085939 A2 | 6/2016 |
| WO | WO 2017035077 A1 | 3/2017 |
| WO | WO 2017035082 A1 | 3/2017 |
| WO | WO 2017147617 A1 | 8/2017 |
| WO | WO 2017196881 A1 | 11/2017 |
| WO | WO-2017214201 A1 | 12/2017 |

(56) References Cited

FOREIGN PATENT DOCUMENTS

| WO | WO 2018039192 A1 | 3/2018 |
|---|---|---|
| WO | WO 2018039197 A1 | 3/2018 |
| WO | WO-2018064354 A1 | 4/2018 |
| WO | WO 2018170476 A1 | 9/2018 |
| WO | WO-2019075136 A1 | 4/2019 |
| WO | WO-2020018498 A1 | 1/2020 |
| WO | WO-2020028820 A1 | 2/2020 |
| WO | WO-2020033344 A1 | 2/2020 |
| WO | WO-2020068986 A1 | 4/2020 |
| WO | WO-2020072621 A1 | 4/2020 |
| WO | WO-2020118045 A1 | 6/2020 |

OTHER PUBLICATIONS

Acland et al., "Gene Therapy Restores Vision in a Canine Model of Childhood Blindness," Nature Genetics, 28(1):92-95 (2001).

Aharony, D. et al., "Pharmacological characterization of cloned human NK-2 (neurokinin A) receptor expressed in a baculovirus/Sf-21 insect cell system," Molecular Pharmacology, 44(2):356-363 (1993).

Akturk, S. et al., "Nitric oxide and malondialdehyde levels in plasma and tissue of psoriasis patients," Journal of the European Academy of Dermatology and Venereology, 26(7):833-837 (2012).

Albano et al., "Immune response towards lipid peroxidation products as a predictor of progression of non-alcoholic fatty liver disease to advanced fibrosis," Gut 54:987-93 (2005).

Aldeyra Press Release Phase II Allergic Conjunctivitis, Feb. 29, 2016 (3 pages).

Aldeyra Press Release—Positive Results From Phase II Clinical Trial in Subjects With Noninfectious Anterior Uveitis, May 9, 2016 (4 pages).

Aldini et al., "Lipoxidation-Derived Reactive Carbonyl Species as Potential Drug Targets in Preventing Protein Carbonylation and Related Cellular Dysfunction," ChemMedChem, 1(10):1045-1058 (2006).

Aldini et al., "The carbonyl scavenger carnosine ameliorates dyslipidaemia and renal function in Zucker obese rats," The Journal of Cellular and Molecular Medicine, 15(6):1339-1354 (2011).

Al-Essa et al., "Clinical, fluorine-18 labeled 2-fluoro-2-deoxyglucose positron emission tomography (FDG PET), MRI of the brain and biochemical observations in a patient with 4-hydroxybutyric aciduria; a progressive neurometabolic disease," Brain Dev., 22(2):127-31 (2000).

Al-Hasani, H. et al., "Phosphoryl exchange is involved in the mechanism of the insulin receptor kinase," FEBS Lett., 349:17-22 (1994).

Amara et al., "Autoantibodies to malondialdehyde-modified epitope in connective tissue disease and vasculitides," Clinical and Experimental Immunology, 101(2):233-238 (1995).

Ao et al., "Methyl-β-Cyclodextrin Impairs the Monocyte-Adhering Ability of Endothelial Cells by Down-Regulating Adhesion Molecules and Caveolae and Reorganizing the Actin Cytoskeleton," Biol Pharm Bull, 39(6):1029-1034 (2016).

Apparsundaram, S. et al., "Molecular cloning of a human, hemicholinium-3-sensitive choline transporter," Biochem. Biophys. Res. Commun., 276(3):862-867 (2000).

Ardati, A. et al., "Interaction of [3H] orphanin FQ and 125I-Tyr14-orphanin FQ with the orphanin FQ receptor: kinetics and modulation by cations and guanine nucleotides," Mol. Pharmacol., 51:816-824 (1997).

Ashton et al., "Location of penetration and metabolic barriers to levobunolol in the corneal epithelium of the pigmented rabbit," The Journal of Pharmacology and Experimental Therapeutics, 259(2):719-724 (1991).

Atkinson et al., "Triazaphenanthrenes. Part VI.* Further Observations on the Widman-Stoermer and Brosche Reactions," J. Chem. Soc. (C) pp. 2053-2060 (1966).

Augustin et al., "Oxidative reactions in the tear fluid of patients suffering from dry eyes," Graefe's Archive for Clinical and Experimental Ophthalmology, 233 (11):694-698 (1995).

Axelsson et al., "Experimental colitis induced by dextran sulphate sodium in mice: beneficial effects of sulphasalazine and olsalazine," Aliment Pharmacol Ther, 12:925-934 (1998).

Bachman, G.B. et al., "Quinoline derivatives from 3-nitro-4-hydroxyquinoline," Am. Chem. Soc., 69:365-371 (1947).

Balci et al., "Effects of computer monitor-emitted radiation on oxidant/antioxidant balance in cornea and lens from rats," Molec Vis, 15:2521-2525 (2009).

Balci et al., "Investigation of oxidative stress in pterygium tissue," Molecular Vision, 17:443-447 (Feb. 2011).

Ballard, S.A. et al., "Effects of sildenafil on the relaxation of human corpus cavernosum tissue in vitro and on the activities of cyclic nucleotide phosphodiesterase isozymes," J. Urol., 159(6):2164-2171 (1998).

Baltatzis et al., "Mycophenolate mofetil as an immunomodulatory agent in the treatment of chronic ocular inflammatory disorders," Ophthalmology, 110(5):1061-5 (May 2003).

Bardwell, A.J. et al., "Docking sites on mitogen-activated protein kinase (MAPK) kinases, MAPK phosphatases and the Elk-1 transcription factor compete for MAPK binding and are crucial for enzymic activity," Biochem. J., 370:1077-1085 (2003).

Baron, B.M. et al., "[3H]MDL 105,519, a high-affinity radioligand for the N-methyl-D-aspartate receptor-associated glycine recognition site," J. Pharmacol. Exp. Ther., 279:62-68 (1996).

Bartoli et al., "Malondialdehyde in Exhaled Breath Condensate as a Marker of Oxidative Stress in Different Pulmonary Diseases," Mediators of Inflammation, vol. 2011, Article ID 891752 (2011) (7 pages).

Batista et al., "Age-dependent changes in rat lacrimal gland antioxidant and vesicular related protein expression profiles," Molecular Vision, 18:194-202 (2012).

Batista et al., "Short-term treatment with bisphenol-A leads to metabolic abnormalities in adult male mice," PLOS One, vol. 7, No. 3, (2012).

Baum et al, "Omega 3 fatty acid inhibition of inflammatory cytokine-mediated Connexin43 regulation in the heart," Front. Physiol. 3:272 doi: 10.3389/fphys.2012.00272. eCollection 2012 (2012).

Baz et al., "Plasma reactive oxygen species activity and antioxidant potential levels in rosacea patients: correlation with seropositivity to Helicobacter pylori," International Journal of Dermatology, 43(7):494-497 (2004).

Berge et al., "Pharmaceutical salts," The Journal of Pharmaceuticals Sciences, 66(1):1-19 (1977).

Berkhout, T.A. et al., "Cloning, in vitro expression, and functional characterization of a novel human CC chemokine of the monocyte chemotactic protein (MCP) family (MCP-4) that binds and signals through the CC chemokine receptor 2B,", J. Biol. Chem., 272:16404-16413 (1997).

Bermudez et al., "Thermosensitive poloxamer-based injectables as controlled drug release platforms for veterinary use: Development and in-vitro evaluation," Intl Res J Pharmacy Pharmacol, 1(6):109-118 (Sep. 2011).

Bernstein et al., "Retinal Toxicity Associated with Occupational Exposure to the Fish Anesthetic MS-222," Am J Ophthalmol, 124(6):843-844 (1997).

Bernstein et al., "Mechanism of Action of Aromatic Amines that Short-Circuit the Visual Cycle," Biochemistry, 25(11):3370-3377 (1986).

Bernstein et al., "Short-Circuiting the Visual Cycle with Retinotoxic Aromatic Amines," Proc Natl Acad Sci USA, 83(6):1632-1635 (1986).

Bernstein et al., The Specific Inhibition of 11-cis-retinyl Palmitate Formation in the Frog Eye by Diaminophenoxypentane, an Inhibitor of Rhodopsin Regeneration, Vision Research, 25(6):741-748 (1985).

Bickett, D.A. et al., "A high throughput fluorogenic substrate for interstitial collagenase (MMP-1) and gelatinase (MMP-9)," Anal. Biochem., 212:58-64 (1993).

Bignon, E. et al., "SR146131: a new potent, orally active, and selective nonpeptide cholecystokinin subtype 1 receptor agonist. I. In vitro studies," J. Pharmacol. Exp. Ther. 289:742-751 (1999).

(56) References Cited

OTHER PUBLICATIONS

Bousquet et al., "How to Design and Evaluate Randomized Controlled Trials in Immunotherapy for Allergic Rhinitis: An ARIA-GA2 LEN Statement," Allergy, 66(6):765-774 (2011).
Boyer et al., "Lipofuscin and N-Retinylidene-N-Retinylethanolamine (A2E) Accumulate in Retinal Pigment Epithelium in Absence of Light Exposure," J Biol Chem, 287(26):22276-22286 (Jun. 2012).
Bozkir et al., "Effect of hydroxypropyl-beta-cyclodextrin on the solubility, stability and in-vitro release of ciprofloxacin for ocular drug delivery," Acta Poloniae Pharmaceutica, 69(4):719-24 (2012).
Bragagni et al., "Cyclodextrin complexation highly enhances efficacy of arylsulfonylureido benzenesulfonamide carbonic anhydrase inhibitors as a topical antiglaucoma agents," Bioorganic & Medicinal Chemistry, 23(18):6223-6227) (2015).
Brenneman et al., "Cannabidiol Provides Protection from Ethanol and Ammonium toxicity in a Hippocampal Model of Hepatic Encephalopathy," 24th Annual Symposium of the International Cannabinoid Research Society, Baveno, Italy, Jun. 28-Jun. 3, 2014 (p. 73).
Brenneman et al., "Small Molecule Anticonvulsant Agents with Potent In Vitro Neuroprotection," Journal of Molecular Neuroscience, 47(2):368-379 (2012).
Brewitt et al., "Dry Eye Disease—The Scale of the Problem," Survey of Ophthalmol, 45(Suppl 2): S199-S2 (Mar. 2001).
Brockhaus, M. et al., "Identification of two types of tumor necrosis factor receptors on human cell lines by monoclonal antibodies," Proc. Natl. Acad. Sci. U.S.A., 87:3127-3131 (1990).
Brown, G.B., "3H-batrachotoxinin-A benzoate binding to voltage-sensitive sodium channels: inhibition by the channel blockers tetrodotoxin and saxitoxin," J. Neurosci., 6:2064-2070 (1986).
Brozek et al., "Grading quality of evidence and strength of recommendations in clinical practice guidelines: Part 2 of 3. The GRADE approach to grading quality of evidence about diagonstic tests and strategies," Allergy, 64(8):1109-1116 (2009).
Bryant, H.U. et al., "A novel class of 5-HT2A receptor antagonists: aryl ammoguanidines," Life Sci., 59(15):1259-1268 (1996).
Bucciantini et al., "Inherent Toxicity of Aggregates Implies a Common Mechanism for Protein Misfolding Diseases," Nature, 416(6880):507-511 (2002).
Buchan, K.W. et al., "Characterization of three non-peptide endothelin receptor ligands using human cloned ETA and ETB receptors," Brit. J. Pharmacol., 112:1251-1257 (1994).
Buddi et al., "Evidence of oxidative stress in human corneal diseases," The Journal of Histochemistry and Cytochemistry: official journal of the Histochemistry Society, 50(3):341-351 (2002).
Bundgaard et al., "Glycolamide esters as biolabile prodrugs of carboxylic acid agents: Synthesis, Stability, bioconversion, and physicochemical properties," Journal of Pharmaceutical Sciences, 77(4):285-298 (1988).
Bundgaard, "Mean to enhance penetration: (1) Prodrugs as a means to improve the delivery of peptide drugs," Advanced Drug Delivery Review, 8(1):1-38 (1992).
Burcham et al., "Aldehyde-Sequestering Drugs: Tools for Studying Protein Damage by Lipid Peroxidation Products," Toxicology, 181-182:229-236 (2002).
Burstein, "Preservative cytotoxic threshold for benzalkonium chloride and chlorhexidine digluconate in cat and rabbit corneas," Investigative Ophtalmology and Visual Science, 19(3):308-313 (1980)
Burstein, "The effects of topical drugs and preservatives on the tears and corneal epithelium in dry eye," Transactions of the Ophthalmological Societies of the United Kingdom, 104:402-409 (1985).
Canonica et al., "Recommendations for standardization of clinical trials with Allergen Specific Immunotherapy for respiratory allergy. A statement of a World Allergy Organization (WAO) taskforce," Allergy, 62(3):317-324 (2007).
Canonica et al., "Sub-lingual immunotherapy: World Allergy Organization Position Paper 2009," Allergy, 64(Suppl 91:1-59 (2009).
Casanaro et al., "A convenient solvent system for cellulose dissolution and derivatization. Mechanistic aspects of the acylation of the biopolymer in tetraallylammonium fluoride/dimethyl sulfoxide," Carbohydrate Polymers, 8(3):1395-1402 (2011).
Casanaro et al., "Efficacy of vigabatrin intervention in a mild phenotypic expression of succinic semialdehyde dehydrogenase deficiency," JIMD Rep. 2:119-23 (2011).
Cejkova et al., "The role of conjunctival epithelial cell xanthine oxidoreductase/xanthine oxidase in oxidative reactions on the ocular surface of dry eye patients with Sjögren's syndrome," Histol Histopathol 22(9):997-1003 (Sep. 2007).
Cesura et al., "Characterization of the binding of [3H]Ro 41-1049 to the active site of human monoamine oxidase-A," Mol. Pharmacol., 37:358-366 (1990).
Chapple et al., "Unfolding Retinal Dystrophies: a Role for Molecular Chaperones?" Trends Mol Med, 7(9):414-421 (2001).
Chen et al., "Methazolamide Calcium Phosphate Nanoparticles in an Ocular Delivery System," Pharm Soc Japan, 130(3):419-24 (2010).
Cheng et al., "A synthetic peptide derived from p34cdc2 is a specific and efficient substrate of src-family tyrosine kinases," J. Biol. Chem., 267:9248-9256 (1992).
Chiarpotto et al., "Role of 4-hydroxy-2,3-nonenal in the pathogenesis of fibrosis," Biofactors, 24(1-4):229-36 (2005).
Chicchi et al., "Alterations in receptor activation and divalent cation activation of agonist binding by deletion of intracellular domains of the glucagon receptor," J. Biol. Chem., 272:7765-7769 (1997).
Choi et al., "The human serotonin 5-HT2B receptor: pharmacological link between 5-HT2 and 5-HT1D receptors," FEBS Lett., 352:393-399 (1994).
Choi et al., "Expression of Lipid Peroxidation Markers in the Tear Film and Ocular Surface of Patients with Non-Sjogren Syndrome: Potential Biomarkers for Dry Eye Disease," Curr Eye Res, 41(9):1143-11 (2016).
Clark et al., "Inhibition of dexamethasone-induced cytoskeletal changes in cultured human trabecular meshwork cells by tetrahydrocortisol," Invest. Ophtalmol. Vis. Sci., 37:805-813 (1996).
ClinicalTrials.gov identifier NCT02578914, "A Safety and Activity Study of NS2 in Subjects with Allergic Conjunctivitis," https://clinicaltrials.gov/ct2/show/NCT02578914 (6 pages) (2015).
Clinical Trials Results for Outcome Measures of Ocular Itching and Ocular Tearing (1 page) (2016).
ClinicalTrials.gov identifier NCT02406209, "A Safety and Efficacy Study of NS2 in Patients with Anterior Uveitis," https://clinicaltrials.gov/ct2/show/NCT02406209 (4 pages) (2015).
Clinical Trials Results of Treatment with Aldehyde Trapping Compound NS2 (1 page) (2015).
ClinicalTrials.gov identifier NCT02402309, "A Study of Topical NS2 Cream to Treat Ichthyosis in Sjogren-Larsson Syndrome (SLS)," https://clinicaltrials.gov/ct2/show/NCT02402309 (3 pages) (2015).
Clinical Trials Results of Treatment with NS2 Topical Formulation (1 page) (2015).
Conover et al., "Thiazole Analogs of Pyridoxine," Journal of the American Chemical Society, 72(11):5221-5225 (1950).
Cooper et al., "Clinicopathologic study of dextran sulfate sodium experimental murine colitis," Lab Invest, 69(2):238-49 (Aug. 1993).
Couvineau et al., "Molecular identification and structural requirement of vasoactive intestinal peptide (VIP) receptors in the human colon adenocarcinoma cell line, HT-29," Biochem. J., 231:139-143 (1985).
Cullen et al, "Administration of the small molecule aldehyde trap NS2 in a hamster model of radiation-induced oral mucositis," ISOO 2015 Annual Meeting Abstract, Support Care Cancer, 23 (Suppl 1): S107 (Jun. 2015).
Cullen et al, "The small molecule aldehyde trap NS2 exhibits potent anti-inflammatory activity in three murine models of inflammation," AAAAI Annual Meeting Abstract, 1 page (Feb. 2015).
De Jong, "Age-Related Macular Degeneration," N Engl J Med, 355(14):1474-1485 (2006).
Del Valle, "Cyclodextrins and their uses: a review," Process Biochemistry, 39(9):1033-1046 (2004).

(56) References Cited

OTHER PUBLICATIONS

Demir et al., "The protective effect of alpha-lipoic acid against oxidative damage in rabbit conjunctiva and cornea exposed to ultraviolet radiation," Ophthalmologica, 219(1):49-53 (Jan.-Feb. 2005).
Demir et al., "Oxidative stress of intracameral lidocaine and levobupivacaine on ocular tissues," Br J Ophthalmol, 94(8):1083-7 (Aug. 2010).
Dente et al., "Modified phage peptide libraries as a tool to study specificity of phosphorylation and recognition of tyrosine containing peptides," J. Mol. Biol., 269:694-703 (1997).
Devedjian et al., "Further characterization of human alpha 2-adrenoceptor subtypes: [31-1]RX821002 binding and definition of additional selective drugs," Eur. J. Pharmacol., 252:43-49 (1994).
Dolmotova et al, "Cardiomyocyte ATP release through pannexin 1 aids in early fibroblast activation," Am. J. Physiol Heart Circ Physiol 303(10):H1208-1218 (2012).
Dorje et al., "Antagonist binding profiles of five cloned human muscarinic receptor subtypes," J. Pharmacol. Exp. Ther., 256:727-733 (1991).
Dowling, "Neural and Photochemical Mechanisms of Visual Adaptation in the Rat," Journal of General Physiology, 46(6):1287-1291 (1963).
Drysdale et al., "Complex Promoter and Coding Region Beta 2-adrenergic Receptor Haplotypes Alter Receptor Expression and Predict in vivo Responsiveness," Proc Natl Acad Sci USA, 97(19):10483-10488 (2000).
Egger, et al., "Keratinocyte growth factor ameliorates dextran sodium sulfate colitis in mice," Dig Dis Sci, 44(4): 836-44 (Apr. 1999).
Ellman et al., "A new and rapid colorimetric determination of acetylcholinesterase activity," Biochem. Pharmacol., 7: 88-95 (1961).
Erdos et al, "Neutral endopeptidase 24.11 (enkephalinase) and related regulators of peptide hormones," FASEB J. 3:145 (1989).
Ermolieff et al., "Proteolytic activation of recombinant pro-memapsin 2 (pro-beta-secretase) studied with new fluorogenic substrates," Biochemistry, 39:12450-12456 (2000).
Escalera et al., "Succinic semialdehyde dehydrogenase deficiency: decrease in 4-OH-butyric acid levels with low doses of vigabatrin," An Pediatr (Barc). 72(2): 128-32 (2010).
Esterbauer et al., "Chemistry and Biochemistry of 4-Hydroxynonenal, Malonaldehyde and Related Aldehydes," Free Radic Biol Med, 11:81-128 (1991).
European Supplementary Partial Search Report issued by the European Patent Office for European Patent Application No. 13865015.5 dated Mar. 31, 2016 (9 pages).
European Supplementary Partial Search Report issued by the European Patent Office for European Patent Application No. 14743711.5 dated Jul. 20, 2016 (14 pages).
Everest-Todd, "Topical Application of Cyclodextrin Ethers in the Control of Pain," Proceedings of the Eighth International Symposium on Cyclodextrins, pp. 495-498 (1998).
FDA, "BAM R59: Phosphate-Buffered Saline (PBS), pH 7.4," Jan. 2001, retrieved online at <http://www.fda.gov/Food/FoodScienceR. esearch/LaboratoxyMethods/ucm062268.htm> on Apr. 18, 2015 (1 page).
Feighner et al., "Receptor for motilin identified in the human gastrointestinal system," Science, 284:2184-2188 (1999).
Fernandes et al., "Characterization of angiotensin-converting enzymes 1 and 2 in the soleus and plantaris muscles of rats," Braz J Med Biol Res., 43:837-842 (2010).
Ferry et al., "Binding of prostaglandins to human PPARγ: Tool assessment and new natural ligands," Eur. J. Pharmacol., 417:77-89 (2001).
Feve et al., "Transcriptional down-regulation by insulin of the beta 3-adrenergic receptor expression in 3T3-F442A adipocytes: a mechanism for repressing the cAMP signaling pathway," Proc Natl Acad Sci USA. 91:5677 (1994).
Fiske et al., "The Colormetric Determination of Phosphorus," J. Biol. Chem., 66:375-400(1925).

Fitzmaurice et al., "Aldehyde dehydrogenase inhibition as a pathogenic mechanism in Parkinson disease," Proc. Natl Acad Sci U.S.A, 110(2):636-641 (2013).
Ford et al., "Pharmacological pleiotropism of the human recombinant alphalA-adrenoceptor: implications for alpha1-adrenoceptor classification," Brit. J. Pharmacol., 121:1127-1135 (1997).
Fowler et al., "Coloured Complexes of all-trans-retinal with Benzocaine and Other Local Anesthetics," J Photochem Photobiol B, 8(2):183-188 (1991).
Frantz et al., "The Activation State of p38 Mitogen-Activated Protein Kinase Determines the Efficiency of ATP Competition for Pyridinylimidazole Inhibitor Binding," Biochemistry, 37:13846-13853 (1998).
Friesen et al., "Optimization of a Tertiary Alcohol Series of Phosphodiesterase-4 (PDE4) Inhibitors: Structure-Activity Relationship Related to PDE4 Inhibition and Human Ether-a-go-go Related Gene Potassium Channel Binding Affinity," J. Med. Chem., 46(12):2413-2426 (2003).
Fuchs et al., "Functional characterization of three mutations of the endothelin B receptor gene in patients with Hirschsprung's disease: evidence for selective loss of Gi coupling," Mol. Med., 7:115-124 (2001).
Fukunaga et al., "Single nucleotide polymorphism of human platelet-activating factor receptor impairs G-protein activation," J. Biol. Chem., 276:43025-43030 (2001).
Full 1H NMR assignment for RAL-NS2 in CDCIJ, submitted to Japanese Patent Office Mar. 1, 2012.
Ganapathy et al., "Molecular and ligand-binding characterization of the sigma-receptor in the Jurkat human T lymphocyte cell line," JPET, 289:251-260 (1999).
Gasper et al., "2-Hydroxypropyl-beta-cyclodextrin (HPβCD) reduces age-related lipofuscin accumulation through a cholesterol-associated pathway," Scientific Reports, 7(2197):1-7 (2017).
Gibson et al., "Stable isotope dilution analysis of 4-hydroxybutyric acid: an accurate method for quantification in physiological fluids and the prenatal diagnosis of 4-hydroxybutyric aciduria," Biomed Environ Mass Spectrom., 19(2):89-93 (1990).
Gibson et al., "Stable-isotope dilution analysis of D- and L-2-hydroxyglutaric acid: application to the detection and prenatal diagnosis of D- and L-2-hydroxyglutaric acidemias," Pediatr Res., 34(3):277-80 (1993).
Gibson et al., "The Aldehyde Trap NS2 Mitigates Dense Haze in a Rabbit Model of Photorefractive Keratectomy" ARVO Annual Meeting Abstract, 1 page (Jun. 2015).
Godard et al., "Sur les orthoamino formyl quinoleines, nouveaux synthons heterocycliques," J Heterocyclic Chem, 17(3):465-473 (1980).
Gomez, "Dimethyltin(IV) 2,6-disubstituted pyridine complexes," J. Organometallic Chemistry, 672(2):115-122 (2003).
Good, "Measuring field loss in children administered vigabatrin: a problem in search of a solution," J AAPOS. 15(5):411-2 (2011).
Gopalakrishnan et al., "Stable expression, pharmacologic properties and regulation of the human neuronal nicotinic acetylcholine alpha 4 beta 2 receptor," J. Pharmacol. Exp. Ther., 276:289-297 (1996).
Gould et al., "[3H]nitrendipine-labeled calcium channels discriminate inorganic calcium agonists and antagonists," Proc. Natl. Acad. Sci. U.S.A., 79:3656-3660 (1982).
Grandy et al., "Cloning of the cDNA and gene for a human D2 dopamine receptor," Proc. Natl. Acad. Sci. U.S.A., 86:9762-9766 (1989).
Green et al., "Influence of Various Agents on Corneal Permeability," American Journal of Ophthalmology, 72(5):897-905 (1971).
Green et al., "Characterization of [(3)H]-CGP54626A binding to heterodimeric GABA(B) receptors stably expressed in mammalian cells," Brit. J. Pharmacol., 131:1766-1774 (2000).
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950).
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950) [Machine Translation].

(56) References Cited

OTHER PUBLICATIONS

Gromachevskaya et al., "4H-3,1-benzoxazines. 2. Synthesis of 2,4-substituted 1,2-dihydro-4H-3,1-benzoxazines," Chemistry of Heterocyclic Compounds, 24(6):692-697 (Jun. 1988).

Grotto et al., "Importance of the lipid peroxidation biomarkers and methodological aspects for malondialdehyde quantification," Quim Nova, 32(1):169-174 (2009).

Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, 2 pages (Jul. 2018).

Hampson et al., "Cannabidiol and (-)Delta9-tetrahydrocannabinol are neuroprotective antioxidants," Proc. Nat. Acad. Sci 95:8268-8273 (1998).

Hassan et al., "Oxidative stress in systemic lupus erythematosus and rheumatoid arthritis patients: relationship to disease manifestations and activity," International Journal of Rheumatic Diseases, 14(1):325-331 (2011).

Herbort et al., "Endotoxin-induced uveitis in the rat," Graefe's Arch Clin Exp Ophthalmol, 226:553-8 (1988).

Heuillet et al., "Characterization of a Human NK1 Tachykinin Receptor in the Astrocytoma Cell Line U 373 MG ," J. Neurochem., 60:868-876 (1993).

Highlights of Prescribing Information, Bridion® (sugammadex) Injection, for intravenous use, Initial U.S. Approval: 2015, Last Revised Dec. 2015 (19 pages).

Hogema et al., "Pharmacologic rescue of lethal seizures in mice deficient in succmate semialdehyde dehydrogenase," Nat Genet. 29:212-16 (2001).

Hope et al., "Characterization of a human 5-hydroxytryptamine3 receptor type A (h5-HT3R-AS) subunit stably expressed in HEK 293 cells," Brit. J. Pharmacol., 118:1237-1245 (1996).

Horner et al., "Analogs of 3-Amino-7-chloro-1,2,4-benzotriazine 1-Oxide as Antimalarial Agents," J. Med. Chem., 11(5):946-949 (1968).

Hoyer et al., "Characterization of the 5-HT1B recognition site in rat brain: binding studies with (-)[125I]iodocyanopindolol," Eur. J. Pharmacol., 118:1-12 (1985).

Huang et al., "Identification of human Ether-à-go-go related gene modulators by three screening platforms in an academic drug-discovery setting," Assay Drug Dev Technol., 8(6):727-42 (2010).

Huang et al., "Novel peptide inhibitors of angiotensin-converting enzyme 2," J. Biol. Chem., 278:15532-15540 (2003).

Hubbard, "Geometrical Isomerization of Vitamin A, Retinene and Retinene Oxime," Journal of the American Chemical Society, 78(18):4662-4667 (1956).

Hugues et al., "Preparation of a pure monoiodo derivative of the bee venom neurotoxin apamin and its binding properties to rat brain synaptosomes," J. Biol. Chem., 257:2762-2769 (1982).

Hurd et al., "Reaction of Propiolactone with Aniline Derivatives," Journal of the American Chemical Society, 74(23):5889-5893 (1952).

Inoue et al., "Filter-binding assay procedure for thyroid hormone receptors," Anal Biochem. 134(1):176 (1983).

International Preliminary Report on Patentability issued in PCT/US2016/048054 dated Feb. 27, 2018 (5 pages).

International Preliminary Report on Patentability issued in PCT/US2016/048064 dated Feb. 27, 2018 (6 pages).

International Preliminary Report on Patentability issued by the Korean Intellectual Property Office as International Searching Authority for International Application No. PCT/US2013/076592 dated Jun. 23, 2015 (6 pages).

International Preliminary Report on Patentability issued by the Korean Intellectual Property Office as International Searching Authority for International Application No. PCT/US2014/012356 dated Jul. 28, 2015 (7 pages).

International Preliminary Report on Patentability issued by the United States Patent and Trademark Office as International Searching Authority for International Application No. PCT/US2014/012762 dated Jul. 28, 2015 (8 pages).

International Preliminary Report on Patentability issued by the European Patent Office as International Searching Authority for International Application PCT/US2006/020320 dated Nov. 30, 2007 (8 pages).

International Search Report and Written Opinion issued in PCT/US2006/020320, dated Sep. 26, 2006 (10 pages).

International Search Report and Written Opinion issued by the United States Patent and Trademark Office as International Searching Authority for International Application No. PCT/US2017/047945 dated Oct. 20, 2017 (9 pages).

International Search Report and Written Opinion issued in PCT/US2016/048054 dated Nov. 4, 2016 (7 pages).

International Search Report and Written Opinion issued in PCT/US2016/048064 dated Nov. 15, 2016 (8 pages).

International Search Report and Written Opinion issued by the United States Patent and Trademark Office as International Searching Authority for International Application No. PCT/US2010/059719 dated Feb. 8, 2011 (7 pages).

International Search Report and Written Opinion issued by the Korean Intellectual Property Office as International Searching Authority for International Application No. PCT/US2013/076592 dated Apr. 30, 2014 (10 pages).

International Search Report and Written Opinion issued by the Korean Intellectual Property Office as International Searching Authority for International Application No. PCT/US2014/012356 dated May 30, 2014 (11 pages).

International Search Report and Written Opinion issued by the United States Patent and Trademark Office as International Searching Authority for International Application No. PCT/US2014/012762 dated Jul. 18, 2014 (11 pages).

International Search Report and Written Opinion issued by the United States Patent and Trademark Office as International Searching Authority for International Patent Application No. PCT/US2017/020020 dated May 24, 2017 (12 pages).

International Search Report and Written Opinion issued by the United States Patent and Trademark Office as International Searching Authority for International Patent Application No. PCT/US2017/031808 dated Aug. 11, 2017.

International Search Report and Written Opinion issued by the United States Patent and Trademark Office as International Searching Authority for International Patent Application No. PCT/US2017/047958 dated Oct. 31, 2017.

International Search Report and Written Opinion issued by the United States Patent and Trademark Office as International Searching Authority for International Patent Application No. PCT/US2018/023000 dated Jun. 1, 2018 (8 pages).

International Search Report and Written Opinion issued by the United States Patent and Trademark Office as International Searching Authority for International Patent Application No. PCT/US2018/055310 dated Jan. 29, 2019 (9 pages).

Iriyama et al., "A2E, a pigment of the lipofuscin of retinal pigment epithelial cells, is an endogenous ligand for retinoic acid receptor," J Biol Chem., 283(18):11947-53 (2008) Epub Mar. 6, 2008.

Ishida et al., "Stabilization of calmodulin-dependent protein kinase II through the autoinhibitory domain," J Biol. Chem., 270:2163-2170 (1995).

Ito et al., "A Medium-Term Rat Liver Bioassay for Rapid in vivo Detection of Carcinogenic Potential of Chemicals," Cancer Science, 94(1):3-8 (2003).

Itokawa et al., "Antiangiogenic effect by SU5416 is partly attributable to inhibition of Flt-1 receptor signaling," Mol. Cancer Ther., 1:295-302 (2002).

Jafari et al., "Evaluation of plasma, erythrocytes, and bronchoalveolar lavage fluid antioxidant defense system in sulfur mustard-injured patients," Clin Toxicol (Phila)., 48(3):184-92 (2010).

Janowski et al., "Structural requirements of ligands for the oxysterol liver X receptors LXRalpha and LXRbeta," Proc. Natl. Acad. Sci. USA, 96:266-271 (1999).

Jarrett et al., "Mitochondrial DNA damage and impaired base excision repair during epileptogenesis," Neurobiology of Disease, 30(1):130-138.

(56) References Cited

OTHER PUBLICATIONS

Ji et al., "Exploration of diverse hinge-binding scaffolds for selective Aurora kinase inhibitors," Bioorg. & Med. Chem. Let. 22:4528 (2012).
Johannsdottir et al., "Development of a Cyclodextrin-Based Aqueous Cyclosporin a Eye Drop Formulations," International Journal of Pharmaceutics, 493(1-2):86-95 (2015).
Johnson et al., "2-Hydroxypropyl-β-Cyclodextrin Removes All-Trans Retinol from Frog Rod Photoreceptors in a Concentration-Dependent Manner," Journal of Ocular Pharmacology and Therapeutics, 26(3):245-248 (2010).
Joseph et al., "Binding of (-)-[3H]-CGP12177 at two sites in recombinant human beta 1-adrenoceptors and interaction with beta-blockers," Naun.-Sch. Arch. Pharm., 369:525-532 (2004).
Kam et al., "Topical Cyclodextrin Reduces Amyloid Beta and Inflammation Improving Retinal Function in Ageing Mice," Experimental Eye Research, 135:59-66 (2015).
Kamino et al., "Deficiency in mitochondrial aldehyde dehydrogenase increases the risk for late-onset Alzheimer's disease in the Japanese population," Biochemical and Biophysical Research Communications, 273(1):192-196 (2000).
Karahashi et al., "Changes of caspase activities involved in apoptosis of a macrophage-like cell line J774.1/JA-4 treated with lipopolysaccharide (LPS) and cycloheximide," Biol. Pharm. Bull., 23:140-144 (2000).
Karan et al., Lipofuscin Accumulation, Abnormal Electrophysiology, and Photoreceptor Degeneration in Mutant ELOVL4 Transgenic Mice: A Model for Macular Degeneration, Proc Natl Acad Sci USA, 102(11):4164-4169 (2005).
Katugampola et al., "[(125)I]-(Pyr(1))Apelin-13 is a novel radioligand for localizing the APJ orphan receptor in human and rat tissues with evidence for a vasoconstrictor role in man," Brit. J. Pharmacol., 132:1255-1260 (2001).
Kenney et al., "The Cascade Hypothesis of Keratoconus," Contact Lens & Ant Eye, 26:139-146 (2003).
Keri, "Rosacea," Merck Manual, Professional Version, https://www.merckmanuals.com/professional/dermatologic-disorders/acne-and-related-disorders/rosacea, 7 pages (2017).
Knapp et al., "Intraocular Availability of Topically Applied Mycophenolate Mofetil in Rabbits," J. Ocul. Pharmacol. Ther., 19(2):181-192 (2003).
La Rosa et al., "Allergic conjunctivitis: a comprehensive review of the literature," Ital J Pediatr, 39:18 (2013).
Landor et al., "Allenes. Part 49, 4-Amino-2-(1-hydroxyalkyl)quinolones from Phenylhydroxylamine and Allenic Nitrites," J Chem Soc Perkin Trans 1, pp. 251-254 (1989).
Langin et al., "[31-1]RX821002: a new tool for the identification of alpha 2A-adrenoceptors," Eur. J. Pharmacol., 167: 95-104 (1989).
Lankin et al., "Role of Oxidative Stress in the Genesis of Atherosclerosis and Diabetes Mellitus: A Personal Look Back on 50 Years of Research," Curr. Aging Sci. 10:18 (2017).
Le et al., "Ligand binding and functional properties of human angiotensin AT1 receptors in transiently and stably expressed CHO-K1 cells," Eur. J. Pharmacol., 513:35-45 (2005).
Lee et al., "Human recombinant soluble guanylyl cyclase: expression, purification, and regulation," Proc. Natl. Acad. Sci. USA, 97(20):10763-10768 (2000).
Lee et al., "The human brain cholecystokinin-B/gastrin receptor. Cloning and characterization," J. Biol. Chem., 268 : 8164-8169 (1993).
Leibundgut et al., "Oxidation-specific epitopes and immunological responses: Translational biotheranostic implications for atherosclerosis," Current Opinion in Pharmacology, 13(2):168-179 (2013).
Leonardi et al., "Correlation Between Conjunctival Provocation Test (CPT) and Systemic Allergometric Tests in Allergic Conjunctivitis," Eye, 4:760-764 (1990).
Leurs et al., "Pharmacological characterization of the human histamine H2 receptor stably expressed in Chinese hamster ovary cells," Brit. J. Pharmacol., 112: 847-854.

Levin et al., "The myocardium-protective Gly-49 variant of the beta 1-adrenergic receptor exhibits constitutive activity and increased desensitization and down-regulation," J. Biol.Chem., 277:30429-30435 (2002).
Lewin et al., "meta- and para-isothiocyanato-t-butylbicycloorthobenzoate: irreversible ligands of the gamma-aminobutyric acid-regulated chloride ionophore," Mol. Pharmacol., 35:189-194 (1989).
Li et al., "Effect of Vitamin A Supplementation on Rhodopsin Mutants Threonine-17 → Methionine and Proline-347 → Serine in Transgenic Mice and in Cell Cultures," Proc Natl Acad Sci USA, 95(20):11933-11938 (1998).
Liu et al., "Comparison of human, mouse, rat, and guinea pig histamine H4 receptors reveals substantial pharmacological species variation," J. Pharmacol. Exp. Ther., 299:121-130 (2001).
Loftsson et al., "Cyclodextrins in Eye Drop Formulations: Enhances Topical Delivery of Corticosteroids to the Eye," Acta Ophthalmologica Scandinavica, 80(2):144-150 (2002).
Loftsson et al., "Cyclodextrin Microparticles for Drug Delivery to the Posterior Segment of the Eye: Aqueous Dexamethasone Eye Drops," Journal of Pharmacy and Pharmacology, 59(5):629-635 (2007).
Lovenberg et al., "Cloning and functional expression of the human histamine H3 receptor," Mol. Pharmacol., 55:1101-1107 (1999).
Lukas, R.J., "Characterization of curaremimetic neurotoxin binding sites on membrane fractions derived from the human medulloblastoma clonal line, T15671," J. Neurochem., 46:1936-1941 (1986).
Luthin et al., "Characterization of two affinity states of adenosine A2a receptors with a new radioligand, 2-[2-(4-amino-3-[125I]iodophenyl)ethylamino]adenosine," Mol. Pharmacol., 47:307-313 (1995).
MacDonald et al., "Molecular characterization of the melanin-concentrating hormone/receptor complex: identification of critical residues involved in binding and activation," Mol. Pharmacol., 58:217-225 (2000).
MacDonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).
MacDonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).
MacDonald et al., "The novel aldehyde trap, ADX-102, reduces inflammation-mediated lung infiltrate in a mouse model of LPS-induced acute lung injury," 13th World Congress on Inflammation Abstract, p. 192 (Jul. 2017).
MacDonald et al., "Novel Small Molecule Aldehyde Sequestering Agents Demonstrate Broad Therapeutic Potential for Ocular Inflammation," ARVO Annual Meeting Abstract, 2 pages (Jul. 2018).
Mackenzie et al., "Characterization of the human dopamine D3 receptor expressed in transfected cell lines," Eur. J. Pharmacol., 266:79-85 (1994).
Maeda et al., "Involvement of All-trans-retinal in Acute Light-induced Retinopathy of Mice," J Biol Chem, 284(22):15173-83 (May 2009).
Maeda et al., "Primary amines protect against retinal degeneration in mouse models of retinopathies," Nat Chem Biol, 8(2):170-178 (Dec. 2011).
Maguire et al., "Orphan-receptor ligand human urotensin II: receptor localization in human tissues and comparison of vasoconstrictor responses with endothelin-1," Brit. J. Pharmacol., 131:441-446 (2000).
Mantey et al., "Discovery of a high affinity radioligand for the human orphan receptor, bombesin receptor subtype 3, which demonstrates that it has a unique pharmacology compared with other mammalian bombesin receptors," J. Biol. Chem., 272:26062-26071 (1997).
Marnett, "Oxy radicals, lipid peroxidation and DNA damage," Toxicology, 181-182:219-222 (2002).
Martin et al., "Molecular cloning and functional characterization of murine cysteinyl-leukotriene 1 (CysLT(1)) receptors.," Biochem. Pharmacol., 62:1193-1200 (2001).

(56) References Cited

OTHER PUBLICATIONS

Matern et al., "Seizures in a boy with succinic semialdehyde dehydrogenase deficiency treated with vigabatrin (gamma-vinyl-GABA)," J Inherit Metab Dis., 19(3):313-8 (1996).
Maurice et al., "Advances in targeting cyclic nucleotide phosphodiesterases," Nat Rev Drug Discov., 13:290-314(2014).
McCord et al., "Superoxide dismutase. An enzymic function for erythrocuprein (hemocuprein).," J. Biol. Chem., 244: 6049-6055 (1969).
McGinnity et al., "Evaluation of fresh and cryopreserved hepatocytes as in vitro drug metabolism tools for the prediction of metabolic clearance." Drug Metab. Dispos., 32(11):1247-1253 (2004).
McLaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," Clinical Science, 34(10):1245-1251 (2015).
Medline Plus. Macular Degeneration—age-related. (6 pages) (2013).
Meijer et al., "Biochemical and cellular effects of roscovitine, a potent and selective inhibitor of the cyclin-dependent kinases cdc2, cdk2 and cdk5," Eur. J. Biochem., 243:527-536 (1997).
Meng et al., "Cloning and pharmacological characterization of a rat kappa opioid receptor," Proc. Natl. Acad. Sci. U.S.A., 90:9954-9958 (1993).
Mialet et al., "Isolation of the serotoninergic 5-HT4(e) receptor from human heart and comparative analysis of its pharmacological profile in C6-glial and CHO cell lines," Brit. J. Pharmacol., 129:771-781 (2000).
Mittl et al., "Structure of recombinant human CPP32 in complex with the tetrapeptide acetyl-Asp-Val-Ala-Asp fluoromethyl ketone," J. Biol. Chem., 272:6539-6547 (1997).
Monaghan et el., "The distribution of [3H]kainic acid binding sites in rat CNS as determined by autoradiography," Brain Res., 252:91-100 (1982).
Monsma et al., "Cloning and expression of a novel serotonin receptor with high affinity for tricyclic psychotropic drugs," Mol. Pharmacol., 43:320-327 (1993).
Mulheron et al., "Human 5-HT1A receptor expressed in insect cells activates endogenous G(o)-like G protein(s)," J. Biol. Chem., 269:12954-12962 (1994).
Muller-Enoch et al., "[6.7-Dihydroxycoumarin (Aesculetin) as a substrate for catechol-o-methyltransferase (author's transl)]," Z. Naturforsch., 31:280-284 (1976).
Munro et al., "Molecular characterization of a peripheral receptor for cannabinoids," Nature, 365:61-65 (1993).
Murphy et al., "Characterization of quisqualate recognition sites in rat brain tissue using DL-[3H]alpha-amino-3-hydroxy-5-methylisoxazole-4-propionic acid (AMPA) and a filtration assay," Neurochem. Res., 12:775-781 (1987).
Nagase et al., "Design and characterization of a fluorogenic substrate selectively hydrolyzed by stromelysin 1 (matrix metalloproteinase-3)," J. Biol. Chem., 269:20952-20957 (1994).
Nakamura et al., "Involvement of Oxidative Stress on Corneal Epithelial Alterations in a Blink-Suppressed Dry Eye," Investigative Ophthalmology and Visual Science, 48(4):1552-1558 (2007).
Negre-Salvayre et al., "Advanced Lipid Peroxidation End Products in Oxidative Damage to Proteins. Potential Role in Diseases and Therapeutic Prospects for the Inhibitors," Br J Pharmacol, 153(1):6-20 (2008).
Nema et al., "Excipients and Their Use in injectable Products," PDA J Pharm Sci Technol, 51(4):166-171 (1997).
Nerurkar et al., "13-Aryl-Glutaconic Acids. II. Imides of Certain 13-aryl-Glutaconic and Glutaric Acids," J Org Chem, 24(12):2055-2056 (1959).
Niwa et al., "Protein oxidative damage in the stratum corneum: Evidence for a link between environmental oxidants and the changing prevalence and nature of atopic dermatitis in Japan," Br J Dermatol., 149:248 (2003).

Nociari et al., "Beta cyclodextrins bind, stabilize, and remove lipofuscin bisretinoids from retinal pigment epithelium," Proc Natl Acad Sci U.S.A E1402-E1408 (2014).
Noorwez et al., "Pharmacological Chaperone-mediated in Vivo Folding and Stablization of the P23H-Opsin Mutant Associated with Autosomal Dominant Retinitis Pigmentosa," J Biol Chem, 278:14442-14450 (2003).
O'Brien et al., "Aldehyde Sources, Metabolism, Molecular Toxicity Mechanisms, and Possible Effects on Human Health," Crit Rev Toxicol, 35:609-662 (2005).
Obourn et al., "Hormone- and DNA-binding mechanisms of the recombinant human estrogen receptor," Biochemistry 32(24):6229 (1993).
Organisciak et al., "Susceptibility to Retinal Light Damage in Transgenic Rats with Rhodopsin Mutations," Invest Ophthalmol Vis Sci, 44(2):486-492 (2003).
Pacholczyk et al., "Expression cloning of a cocaine- and antidepressant-sensitive human noradrenaline transporter," Nature, 350:350-354 (1991).
Pal et al., "Sulfur mustard analog induces oxidative stress and activates signaling cascades in the skin of SKH-1 hairless mice," Free Radic Biol Med., 47(11):1640-51 (2009).
Palchaudhuri et al., "Corticotropin-releasing factor receptor type 1 from Tupaia belangeri—cloning, functional expression and tissue distribution," Eur. J. Biochem., 258:78-84 (1998).
Parish et al., "Isolation and One-Step Preparation of A2E and iso-A2E, Fluorophores from Human Retinal Pigment Epithelium," Proc Natl Acad Sci USA, 95(25):14609-14613 (1998).
Park et al., "Homogeneous proximity tyrosine kinase assays: scintillation proximity assay versus homogeneous time-resolved fluorescence," Anal. Biochem., 269:94-104 (1999).
Parracho et al., "Differences between the gut microflora of children with autistic spectrum disorders and that of healthy children," Journal of Medical Microbiology, 54:987-991 (2005).
Patel C.Y., "Subtype selectivity of peptide analogs for all five cloned human somatostatin receptors (hsstr 1-5)," Endocrinology, 135:2814-2817 (1994).
Pearl et al., "Inherited disorders of gamma-aminobutyric acid metabolism and advances in ALDH5A1 mutation identification," Dev Med Child Neurol., 57(7):611-617 (2015).
Pellock, "Balancing clinical benefits of vigabatrin with its associated risk of vision loss," Acta Neurologica. Scandinavica. Supplementum., 124(s192):83-91 (2011).
Peralta et al., "Distinct primary structures, ligand-binding properties and tissue-specific expression of four human muscarinic acetylcholine receptors," EMBO. J., 6:3923-3929 (1987).
Petroski et al., "Selective labeling of embryonic neurons cultured on astrocyte monolayers with 5(6)-carboxyfluorescein diacetate (CFDA)," Journal of Neuroscience Methods, 52(1):23-32 (1994).
Pickering, D.S., "Pharmacological characterization of melatonin binding sites in Syrian hamster hypothalamus," Eur. J. Pharmacol., 175:71-77 (1990).
Pontikis et al., "Cyclodextrin alleviates neuronal storage of cholesterol in Niemann-Pick C disease without evidence of detectable blood-brain barrier permeability," Journal of Inherited Metabolic Disease, 36(3):491-498 (2013).
Pozzi et al., "Modification of Collagen IV by Glucose or Methylglyoxal Alters Distinct Mesangial Cell Function," Journal of the American Society of Nephrology, 20:2119-2125 (2009).
Pred Forte Prescribing Information, Allergan, 5 pages (2017).
Pristupa et al., "Pharmacological heterogeneity of the cloned and native human dopamine transporter: disassociation of [3H]WIN 35,428 and [3H]GBR 12,935 binding.," Mol. Pharmacol., 45:125-135 (1994).
Pruneau et al., "LF 16.0335, a novel potent and selective nonpeptide antagonist of the human bradykinin B2 receptor," Brit. J. Pharmacol., 125:365-372 (1998).
Pubchem, SCHEMBL16316728, CID 117758222, Feb. 23, 2016 (13 pages).
Pufahl et al., "Development of a fluorescence-based enzyme assay of human 5-lipoxygenase," Anal. Biochem., 364:204-212 (2007).

(56) References Cited

OTHER PUBLICATIONS

Radu et al., "Treatment with Isotretinoin Inhibits Lipofuscin Accumulation in a Mouse Model of Recessive Stargardt's Macular Degeneration," Proc Natl Acad Sci USA, 100(8):4742-4747(2003).
Radu et al., "Isotretinoin treatment inhibits lipofuscin accumulation in a mouse model of recessive Stargardt's macular degeneration," Novartis Foundation Symposium, 255(51-63):177-178 (2004).
Rapp et al., "The Effects of Local Anaesthetics on Retinal Function," Vision Res, 22(9):1097-1103 (1982).
Rauli et al., "Validation of Malondialdehyde and 4-Hydroxy-2-trans-Nonenal Measurement in Plasma by NICI-GC-MS1," J Biochem, 123:918-923 (1998).
Reed, "Lipid peroxidation and neurodegenerative disease," Free Radical Biology and Medicine, 51(7):1302-1319 (2011).
Rees et al., "Cloning and characterisation of the human 5-HT5A serotonin receptor," FEBS Lett., 355:242-246 (1994).
Reynolds et al., "(-)-[3H] desmethoxyverapamil labels multiple calcium channel modulator receptors in brain and skeletal muscle membranes: differentiation by temperature and dihydropyridines," J. Pharmacol. Exp. Ther., 237: 731-738 (1986).
Rinaldi-Carmona et al., "Characterization of two cloned human CB1 cannabinoid receptor isoforms," J. Pharmacol. Exp. Ther., 278:871-878 (1996).
Rivkees et al., "Identification of domains of the human A1 adenosine receptor that are important for binding receptor subtype-selective ligands using chimeric A1/A2a adenosine receptors," J. Biol. Chem., 270:20485-20490 (1995).
Rizzo et al., "Ichthyosis in Sjögren-Larsson syndrome reflects defective barrier function due to abnormal lamellar body structure and secretion," Arch Dermatol Res, 302(6):443-451 (2010).
Rizzo, "The role of fatty aldehyde dehydrogenase in epidermal structure and function" Dermato-Endocrinol, 3(2):91-99 (2011).
Rizzo et al., "Sjögren-Larsson syndrome: molecular genetics and biochemical pathogenesis of fatty aldehyde dehydrogenase deficiency," Mol Genet Metab. 90(1):1-9 (2007).
Rizzo et al., "Endogenous antioxidants and radical scavengers," Advances in Experimental Medicine and Biology, 698:52-6 (2010).
Roat, "Keratoconjunctivitis Sicca," Merck Manual Professional Version, 5 pages (2016), Available at: https://www.merckmanuals.com/professional/eye-disorders/corneal-disorders/keratoconjunctivitis-sicca.
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Ocular Mucous Membrane Pemphigoid," Merck Manual Professional Version, 3 pages (2016), Available at: https://www.merckmanuals.com/professional/eye-disorders/conjunctival-and-scleral-disorders/ocular-mucous-membrane-pemphigoid.
Roat, "Scleritis," Merck Manual Professional Version, 3 pages (2016), Available at: https://www.merckmanuals.com/professional/eye-disorders/conjunctival-and-scleral-disorders/scleritis.
Roberts et al., "Basic Principles of Organic Chemistry," 2nd edition, copyright 1977 W. A. Benjamin, Inc., pp. 580-582.
Roberts et al., "Experimental Organic Chemistry—A Miniscale Approach," copyright 1994 by Saunders College Publishing, pp. 580-581 and 584-586.
Rohrer et al., "Cloning and characterization of a fourth human somatostatin receptor," Proc. Natl. Acad. Sci. U.S.A. , 90:4196-4200 (1993).
Sahi et al., "Hepatocytes as a tool in drug metabolism, transport and safety evaluations in drug discovery." Current Drug Discov. Technol., 7(3):188-198 (2010).
Salvatore et al., "Molecular cloning and characterization of the human A3 adenosine receptor," Proc. Natl. Acad. Sci. U.S.A., 90:10365-10369 (1993).
Samsonov et al., "Impact of Atherosclerosis- and Diabetes-Related Dicarbonyls on Vascular Endothelial Permeability: A Comparative Assessment," Oxid. Med. Cell Longev. Article 1625130 (2017).

Sandikci et al., "Lipid Peroxidation and Antioxidant Defence System in Patients with Active or Inactive Behcet's Disease," Acta Derm Venereol, 83:342-346 (2003).
Sarafian et al., "Synergistic cytotoxicity of Delta(9)-tetrahydrocannabinol and butylated hydroxyanisole," Toxicology Letters, 133(2-3):171-179 (2002).
Sarup et al., "Resolution of high and low affinity progesterone receptors from human breast carcinoma T47D cells," J. Biol. Chem., 263:5624-5633 (1988).
Sasaki et al., "Retinal drug delivery using eyedrop preparations of poly-L-lysine-modified liposomes,"Eur J Pharm Biopharm, 83(3):364-9 (2013).
Sayed et al., "Metabolic Activation of R,S-1-(Tetrahydro-2-turanyl)-5-fluorouracil (Ftorafur) to 5-fluorouracil by Soluble Enzymes," Cancer Research, 43:4039-4044 (1983).
Schaumberg et al., "Prevalence of Dry Eye Syndrome Among US Women," Am J Ophthalmol, 136(2):318-326 (Aug. 2003).
Schaumberg et al., "Prevalence of Dry Eye Disease among US Men: Estimates from the Physicians' Health Studies," Arch Ophthalmol, 127(6):763-768 (Jun. 2009).
Schioth et al., "Characterization of the binding of MSH-B, HB-228, GHRP-6 and 153N-6 to the human melanocortin receptor subtypes," Neuropeptides, 31:565-571 (1997).
Schramm et al., "The Cross-linked Biopolymer Hyaluronic Acid as an Artificial Vitreous Substitute," Invest Ophthalmol Vis Sci, 53(2):613-621 (Feb. 2012).
Schwinn et al., "Molecular cloning and expression of the cDNA for a novel alpha 1-adrenergic receptor subtype," J. Biol. Chem., 265:8183-8189 (1990).
Sciuto et al., "Therapeutic Treatments of Phosgene-Induced Lung Injury," Inhal Toxicol, 16(8):565-580 (2004).
Search Report and Written Opinion issued by the Intellectual Property Office of Singapore for Singapore Patent Application No. 11201505587Y dated Jul. 12, 2016 (12 pages).
Search Report and Written Opinion issued by the Intellectual Property Office of Singapore for Singapore Patent Application No. 11201504859Y dated Aug. 1, 2016 (12 pages).
Search Report and Written Opinion issued by the Intellectual Property Office of Singapore for Singapore Patent Application No. 11201505599Y dated Sep. 26, 2016 (11 pages).
Serbecic et al., "Anti-oxidative vitamins prevent lipid-peroxidation and apoptosis in corneal endothelial cells," Cell Tissue Res, 320(3):465-75 (Jun. 2005).
Shank et al., "Ion and temperature effects on the binding of gamma-aminobutyrate to its receptors and the high-affinity transport system," J. Neurochem., 54:2007-2015 (1990).
Shen et al., "Molecular cloning and expression of a 5-hydroxytryptamine7 serotonin receptor subtype," J. Biol. Chem., 268:18200-18204 (1993).
Sherman et al., "Cellular Defenses Against Unfolded Proteins: A Cell Biologist Thinks about Neurodegenerative Diseases," Neuron, 29(1):15-32 (2001).
Shipp et al., "Common acute lymphoblastic leukemia antigen (CALLA) is active neutral endopeptidase 24.11 ("enkephalinase"): direct evidence by cDNA transfection analysis," Proc Natl Acad Sci USA. 86:297 (1989).
Shoemaker et al., "[3H]diltiazem binding to calcium channel antagonists recognition sites in rat cerebral cortex," Eur. J. Pharmacol., 111:273-277 (1985).
Siegrist et al., "Radioreceptor assay for alpha-MSH using mouse B16 melanoma cells+.," J. Recep. Res., 8:323-343 (1988).
Sieving et al., "Inhibition of the Visual Cycle in vivo by 13-cis Retinoic Acid Protects from Light Damage and Provides a Mechanism for Night Blindness in Isotretinoin Therapy," Proc Natl Acad Sci USA, 98(4):1835-1840 (2001).
Sills et al., "[3H]CGP 39653: a new N-methyl-D-aspartate antagonist radioligand with low nanomolar affinity in rat brain," Eur. J. Pharmacol., 192:19-24 (1991).
Simeone et al, "Modification of the Pyridine Moiety of Nonpeptidyl Indole GnRH Receptor Antagonists," Bioorganic & Medicinal Chemistry Letters, 12(22):3329-3332 (2002).

(56) References Cited

OTHER PUBLICATIONS

Simonin et al., "The human delta-opioid receptor: genomic organization, cDNA cloning, functional expression, and distribution in human brain," Mol. Pharmacol., 46:1015-1021 (1994).
Smit et al., "Regulation of the human histamine H1 receptor stably expressed in Chinese hamster ovary cells," Brit. J. Pharmacol., 117:1071-1080 (1996).
Smith et al., "Basic pathogenic mechanisms operating in experimental models of acute anterior uveitis," Immunol Cell Biol, 76:497-512 (1998).
Snead et al., "Gamma-hydroxybutyric acid," New England Journal of Medicine, 352(26):2721-2732 (2005).
Snell et al., "Novel structure having antagonist actions at both the glycine site of the N-Methyl-D-Aspartate receptor and neuronal voltage-sensitive sodium channels. Biochemical, electrophysiological, and behavioral characterization," J Pharmacol Exp Ther, 292(1):215-227 (2000).
Spagnol et al., "Efficient synthesis of tricyclic benzobisoxazines by silica gel catalysis," J Org Chem, 2;72(5):1867-1869 (Mar. 2007).
Sparrow et al. "Phospholipid meets all-trans-retinal: the making of RPE bisretmoids," Journal of Lipid Research, 51: 247-261 (2010).
Speth et al., "Benzodiazepine receptors: temperature dependence of [3H]flunitrazepam binding," Life Sci., 24:351-358 (1979).
Stehle et al., "Molecular cloning and expression of the cDNA for a novel A2-adenosine receptor subtype," Mol. Endocrinol., 6:384-393 (1992).
Struys et al., "Determination of the GABA analogue succinic semialdehyde in urine and cerebrospinal fluid by dinitrophenylhydrazine derivatization and liquid chromatography-tandem mass spectrometry: application to SSADH deficiency," J Inherit Metab Dis., 28(6):913-20 (2005).
Struys et al., "Metabolism of gamma-hydroxybutyrate to d-2-hydroxyglutarate in mammals: further evidence for d-2-hydroxyglutarate transhydrogenase," Metabolism, 55(3):353-8 (2006).
Study showing effect of ADX-102 on Fibrotic Changes in Cardiac Fibroblasts Following Cell Stress, American Society for Cell Biology Annual Meeting, Dec. 3-7, 2016 (2 pages).
Sus et al., "Uber die Lichtreaktion der o-Chinondiazide V Mitteilungl) Ubergange heterocyclischer 6-Ringe in heterocyclische 5-Ringe," Liebigs Ann. Chem. 583:150 (1953).
Tahara et al., "Pharmacological characterization of the human vasopressin receptor subtypes stably expressed in Chinese hamster ovary cells," Brit. J. Pharmacol., 125:1463-1470 (1998).
Tang et al., "Effects of four penetration enhancers on corneal permeability of drugs in vitro," Journal of Pharmaceutical Sciences, 83(1):85-90 (1994).
Tatsumi et al., "Pharmacological profile of neuroleptics at human monoamine transporters," Eur. J. Pharmacol., 368 : 277-283 (1999).
Tayeh et al., "Macrophage oxidation of L-arginine to nitric oxide, nitrite, and nitrate. Tetrahydrobiopterin is required as a cofactor," J. Biol. Chem., 264:19654-19658 (1989).
Tewari-Singh et al., "Silibinin attenuates sulfur mustard analog-induced skin injury by targeting multiple pathways connecting oxidative stress and inflammation," PLoS One 7(9):e46149 (2012).
Tian et al., "First total synthesis and determination of the absolute configuration of 1-N-methyl-3-methylamino- [N-butanoicacid-3-(9-methyl-8-propen-7-one)-amide]—benzo [f][1,7]naphthyridine-2-one, a novel benzonaphthyridine alkaloid," Tetrahedron Letters, 53:4892-4895 (2012).
Tikly et al., "Lipid peroxidation and trace elements in systemic sclerosis," Clinical Rheumatology, 25(3):320-324 (2006).
Torkildsen et al., "Efficacy and safety of olopatadine hydrochloride 0.77% in patients with allergic conjunctivitis using a conjunctival allergen-challenge model," Clinical Ophthalmology, 9:1703-1713 (2015).
Toth et al., "A simple, continuous fluorometric assay for HIV protease," Int. J. Pept. Protein Res., 36:544-550 (1990).
Tsugeno et al., "Regions of the molecule responsible for substrate specificity of monoamine oxidase A and B: a chimeric enzyme analysis," J. Biochem., 118 (5) 974-80 (1995).

Tsuzuki et al., "Molecular cloning and expression of the gene encoding human angiotensin II type 2 receptor.," Biochem. Biophys. Res. Commun., 200:1449-1454 (1994).
Tukozkan et al., "Measurement of Total Malondialdehyde in Plasma and tissues by High-Performance Liquid Chromatography and Thiobarbituric Acid Assay," Firat Tip Dergisi, 11(2):88-92 (2006).
Turk et al., "Serum anti-carbonic anhydrase antibodies and oxidant-antioxidant balance in patients with acute anterior uveitis," Ocul Immunol Inflamm, 22(2):127-32 (Apr. 2014).
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Upadhyaya et al., "The sphingolipid degradation product trans-2-hexadecenal forms adducts with DNA," Biochem Biophy Res Comm., 424(1):18-21 (2012).
Vanachayangkul et al., "Inhibition of heme peroxidases by melamine," Enzyme Research, 2012:416062 (2012).
Vignon et al., "[3H]thienyl-phencyclidine ([3H]TCP) binds to two different sites in rat brain. Localization by autoradiographic and biochemical techniques," Brain Res., 378:133-141 (1986).
Vlaskina et al., "Novel Synthesis of Substituted Benzimadazoles by Reduction of of Esters of 4-Alkylamino-3,5-dinitrobenzoic Acids by Tin Chloride," Chemistry Heterocyclic Compounds, vol. 40(4):523-524 (2004).
Vogel et al, "Thirty years beyond discovery—clinical trials in succinic semialdehyde dehydrogenase deficiency, a disorder of GABA metabolism," J Inherit Metab Dis., 36(3):401-10 (2013).
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 277(5):3397-3403 (2002).
Wagner et al., "Omega-conotoxin GVIA binding to a high-affinity receptor in brain: characterization, calcium sensitivity, and solubilization," J. Neurosci., 8:3354-3359 (1988).
Wall et al., "Plant Antitumor Agents. 30. Synthesis and Structure Activity of Novel Camptothecin Analogs," J. Med. Chem., 36(18):2689-2700 (1993).
Walter et al., "Novel Complex N-Heterocycles via Intramolecular 1,5-Electrocyclizations: 1,2,3,4,4a,5,5a,10-Octahydropoyrido-[4",3". 2',3']cyclobutal[1',2':4,5]pyrrolo[2,3-b]pyridines," Heterocycles, 48(8):1581-1591 (1998).
Wang et al., "Markers of oxidative and nitrosative stress in systemic lupus erythematosus: correlation with disease activity," Arthritis and Rheumatism, 62(7):2064-2072 (2010).
Wang et al., "Human mu opiate receptor. cDNA and gemonic clones, pharmacologic characterization and chromosomal assignment," FEBS Lett., 338:217-222 (1994).
Wang, X.K., "Pharmacological study on recombinant human GABA-A receptor complex containing alpha5 (leucine155 to valine) combined with beta3gamma2s subunits," Acta. Pharmacol. Sin., 22:521-523 (2001).
Wang et al., "A facile one-pot synthesis of 2-substituted-3-aminoquinolines: Preparation of benzo[b]naphthyridine-3-carbonitriles," Tetrahedron, 60(13):2937-2942 (2004).
Waslidge et al., "A colorimetric method for the determination of lipoxygenase activity suitable for use in a high throughput assay format," Anal. Biochem., 231:354-358 (1995).
Weishaar et al., "Multiple molecular forms of cyclic nucleotide phosphodiesterase in cardiac and smooth muscle and in platelets. Isolation, characterization, and effects of various reference phosphodiesterase inhibitors and cardiotonic agents," Biochem. Pharmacol., 35:787-800 (1986).
Weng et al., "Insights into the Function of Rim Protein in Photoreceptors and Etiology of Stargardt's Disease from the Phenotype in abcr Knockout Mice," Cell, 98(1):13-23 (1999).
Westphal et al., "Reactions with Piyridinium Pyruvic Acid Esters," Pharmazie, 31(11):770-773 (1976).
Westphal et al., "Reactions with Piyridinium Pyruvic Acid Esters," Pharmazie, 31(11):770-773 (1976) [English Translation].
Wieland et al., "Subtype selectivity and antagonistic profile of the nonpeptide Y1 receptor antagonist BIBP 3226," J. Pharmacol. Exp. Ther., 275:143-149 (1995).

(56) References Cited

OTHER PUBLICATIONS

Witt-Enderby et al., "Characterization and regulation of the human MLIA melatonin receptor stably expressed in Chinese hamster ovary cells," Mol. Pharmacol., 50:166-174 (1996).
Wolkenberg et al., "Design, synthesis, and evaluation of novel 3,6-diaryl-4-aminoalkoxyquinolines as selective agonists of somatostatin receptor subtype 2," J Med Chem, 54(7):2351-2358 (2011).
Wood et al., "The concept of "aldehyde load" in neurodegenerative mechanisms: cytotoxicity of the polyamine degradation products hydrogen peroxide, acrolein, 3-ammopropanal, 3-acetamidiorioanal and 4-aminobutanal in a retinal ganglion cell line," Brain Research, 1145:150-156 (2007).
Wood et al., "Aldehyde Load in Ischemia-Reperfusion by Neutralization of reactive Aldehydes with Phenelzine," Brain Injury: Neuroprotection Brain Res, 1122(1):184-190 (2006).
Wurch et al., "Sequence and functional analysis of cloned guinea pig and rat serotonin 5-HT1D receptors: common pharmacological features within the 5-HT1D receptor subfamily," J. Neurochem., 68:410-418 (1997).
Yadav et al., "Regulation of NF-κB-Induced Inflammatory Signaling by Lipid Peroxidation-Derived Aldehydes," Oxidative Med & Cell Longev, 2013, Art ID 690545, 11 pages (2013).
Yarnell, "Light Flips the Lipid Switch: Palmitoylation—the reversible attachment of palmitate to proteins—gets a new role in vision," C&EN, 82(29):22-23 (2004).
Yokomizo et al., "Hydroxyeicosanoids bind to and activate the low affinity leukotriene B4 receptor, BLT2," J. Biol. Chem., 276:12454-12459 (2001).
Yu et al., "Injectable Chemically Crosslinked Hydrogel for the Controlled Release of Bevacizumab in Vitreous: A 6-Month In Vivo Study," Transl Vis Sci Technol, 4(2,5):1-11 (2015).
Zagol-Ikapitte et al., "Characterization of scavengers of γ-ketoaldehydes that do not inhibit prostaglandin biosynthesis," Chem Res Toxicol, 23(1):240-250 (2010).
Zarkovic, "4-hydroxynonenal and neurodegenerative diseases," Molecular Aspects of Medicine, 24(4-5):293-303 (2003).
Zava et al., "Androgen receptor assay with [3H]methyltrienolone (R1881) in the presence of progesterone receptors," Endocrinology, 104:1007-1012 (1979).
Zhang et al., "Potent nonsteroidal progesterone receptor agonists: synthesis and SAR study of 6-aryl benzoxazines," Bioorg Med Chem Lett, 12(5):787-90 (Mar. 2002).
Zhou et al., "Mechanisms for the induction of HNE-MDA- and AGE-adducts, RAGE and VEGF in retinal pigment epithelial cells," Exp Eye Res., 80(4):567-80 (2005).
Zhou et al., "Chemical and biological evidence for base propenals as the major source of the endogenous M1dG adduct in cellular DNA," J Biol Chem., 280(27):25377-82 (2005).
Zhou et al., "Cloning and expression of human and rat D1 dopamine receptors," Nature, 347:76-80 (1990).
U.S. Appl. No. 16/157,069 of MacDonald et al., filed Oct. 10, 2018.
U.S. Appl. No. 16/168,309 of Chabala et al., filed Oct. 23, 2018.
U.S. Appl. No. 16/300,020 of Brady et al., filed Nov. 8, 2018.
U.S. Appl. No. 16/241,851 of Jordan et al., filed Jan. 7, 2019.
U.S. Appl. No. 16/262,364 of Brady et al., filed Jan. 30, 2019.
U.S. Appl. No. 16/277,865 of Brady et al., filed Feb. 15, 2019.
U.S. Appl. No. 16/374,845 of Machatha et al., filed Apr. 4, 2019.
Mandell et al., "The Aldehyde Trap NS2 Reduces Ocular Inflammation in an Endotoxin-Induced Model in Rats," ARVO Annual Meeting Abstract, 2 pages (Jun. 2015).
Abelson et al., The conjunctival provocation test model of ocular allergy: utility for assessment of an ocular corticosteroid, loteprednol etabonate, J Ocul Pharmacol Ther, 14(6):533-42 (Dec. 1998).
Ackerman et al., "Ocular itch associated with allergic conjunctivitis: latest evidence and clinical management," Ther. Adv. Chronic Dis., 2016; 7(1):52-67.
Al-Bari, "Chloroquine analogues in drug discovery: new directions of uses, mechanisms of actions and toxic manifestations from malaria to multifarious diseases," J Antimicrob Chemother. 2015;70(6):1608-21.

Aldeyra Press Release—Aldeyra Therapeutics Abstract Accepted at 2015 American Academy of Allergy Asthma & Immunology Annual Meeting, Dec. 16, 2014 (2 pages).
Aldeyra Press Release—Aldeyra Therapeutics Abstract Accepted for Presentation at the 2015 Multinational Association of Supportive Care in Cancer—International Society of Oral Oncology (MASCCISOO) Annual Meeting, Apr. 23, 2015 (2 pages).
Aldeyra Press Release—Aldeyra Therapeutics Abstracts Accepted for Presentation at the 2015 Annual Meeting of the Association for Research in Vision and Ophthalmology, Feb. 2, 2015 (2 pages).
Aldeyra Press Release—Aldeyra Therapeutics Announces Agreement with Johnson & Johnson Innovation to Advance Novel Immune-Modulating Drugs for Systemic Inflammatory Diseases, Feb. 27, 2018 (2 pages).
Aldeyra Press Release—Aldeyra Therapeutics Announces Clinical Development Update for Phase 3 Programs, Jan. 25, 2017 (2 pages).
Aldeyra Press Release—Aldeyra Therapeutics Announces Collaboration With the National Organization for Rare Disorders to Enhance Awareness for Sjogren-Larsson Syndrome Patients, Dec. 4, 2014 (2 pages).
Aldeyra Press Release—Aldeyra Therapeutics Announces Development Programs at 2018 Research Day, Jun. 26, 2018 (2 pages).
Aldeyra Press Release—Aldeyra Therapeutics Announces First Patient Enrolled in Allergic Conjunctivitis Phase 2b Clinical Trial, Feb. 7, 2017 (2 pages).
Aldeyra Press Release—Aldeyra Therapeutics Announces First Patient Enrolled in Allergic Conjunctivitis Phase 3 Clinical Trial, Apr. 24, 2018 (2 pages).
Aldeyra Press Release—Aldeyra Therapeutics Announces First Patient Enrolled in Allergic Conjunctivitis Phase IIa Clinical Trial, Sep. 29, 2015 (2 pages).
Aldeyra Press Release—Aldeyra Therapeutics Announces First Patient Enrolled in Dry Eye Disease Phase 2a Clinical Trial, Jun. 6, 2017 (2 pages).
Aldeyra Press Release—Aldeyra Therapeutics Announces First Patient Enrolled in Dry Eye Disease Phase 2b Clinical Trial, Jan. 30, 2018 (2 pages).
Aldeyra Press Release—Aldeyra Therapeutics Announces First Patient Enrolled in Noninfectious Anterior Uveitis Phase 3 Clinical Trial, Apr. 27, 2017 (2 pages).
Aldeyra Press Release—Aldeyra Therapeutics Announces First Patient Enrolled in Noninfectious Anterior Uveitis Phase II Clinical Trial, Apr. 16, 2015 (2 pages).
Aldeyra Press Release—Aldeyra Therapeutics Announces First Patient Enrolled in Sjogren-Larsson Syndrome Phase II Clinical Trial, Mar. 24, 2015 (2 pages).
Aldeyra Press Release—Aldeyra Therapeutics Announces First Patient Enrolled in Sjögren-Larsson Syndrome Pivotal Phase 3 Clinical Trial, Jul. 24, 2018 (2 pages).
Aldeyra Press Release—Aldeyra Therapeutics Announces Last Patient Dosed in Dry Eye Disease Phase 2a Clinical Trial, Jul. 18, 2017 (2 pages).
Aldeyra Press Release—Aldeyra Therapeutics Announces Last Patient Dosed in Dry Eye Disease Phase 2b Clinical Trial, Jul. 12, 2018 (2 pages).
Aldeyra Press Release—Aldeyra Therapeutics Announces Last Patient Dosed in Phase II Trial of NS2 in Patients with Allergic Conjunctivitis, Dec. 16, 2015 (2 pages).
Aldeyra Press Release—Aldeyra Therapeutics Announces Last Patient Dosed in the ALLEVIATE Phase 3 Clinical Trial, Dec. 20, 2018 (2 pages).
Aldeyra Press Release—Aldeyra Therapeutics Announces Positive Mesothelioma Investigator-Sponsored Clinical Trial Results Presented at the International Association for the Study of Lung Cancer 19th World Conference on Lung Cancer, Sep. 25, 2018 (2 pages).
Aldeyra Press Release—Aldeyra Therapeutics Announces Positive Results from Dry Eye Disease Phase 2a Clinical Trial, Sep. 12, 2017 (3 pages).
Aldeyra Press Release—Aldeyra Therapeutics Announces Positive Results from Phase 2b Dry Eye Disease Clinical Trial, Sep. 26, 2018 (2 pages).

(56) References Cited

OTHER PUBLICATIONS

Aldeyra Press Release—Aldeyra Therapeutics Announces Positive Top-Line Results from the Phase 3 ALLEVIATE Trial in Patients with Allergic Conjunctivitis, Mar. 26, 2019 (2 pages).
Aldeyra Press Release—Aldeyra Therapeutics Announces Presentation of Novel Data on the Efficacy of ADX-102 in a Model of Succinic Semialdehyde Dehydrogenase Activity at the 2017 American Society of Human Genetics Annual Meeting, Oct. 5, 2017 (2 pages).
Aldeyra Press Release—Aldeyra Therapeutics Announces Presentation of Phase 2 Allergic Conjunctivitis Results at the 2016 American College of Allergy, Asthma and Immunology Annual Scientific Meeting, Nov. 7, 2016 (2 pages).
Aldeyra Press Release—Aldeyra Therapeutics Announces Presentation of Results on the Efficacy of ADX-102 in Noninfectious Anterior Uveitis at the American Uveitis Society Held at the American Academy of Ophthalmology 2017 Annual Meeting, Oct. 25, 2017 (2 pages).
Aldeyra Press Release—Aldeyra Therapeutics Announces Results from Allergic Conjunctivitis Phase 2b Clinical Trial and Plans for Phase 3 Clinical Testing, Jun. 14, 2017 (3 pages).
Aldeyra Press Release—Aldeyra Therapeutics Announces Third Quarter 2017 Financial Results, Nov. 9, 2017 (4 pages).
Aldeyra Press Release—Aldeyra Therapeutics Launches the Aldeyra Registry for Patients with Sjogren-Larsson Syndrome, Feb. 22, 2017 (2 pages).
Aldeyra Press Release—Aldeyra Therapeutics Opens Enrollment in Noninfectious Anterior Uveitis Phase II Clinical Trial, Mar. 26, 2015 (2 pages).
Aldeyra Press Release—Aldeyra Therapeutics Opens Enrollment in Sjogren-Larsson Syndrome Clinical Trial and Finalizes Noninfectious Anterior Uveitis Clinical Trial Protocol, Mar. 17, 2015 (2 pages).
Aldeyra Press Release—Aldeyra Therapeutics Presents Dry Eye Disease Phase 2a Clinical Trial Results at the Association for Research in Vision and Ophthalmology 2018 Annual Meeting, May 1, 2018 (2 pages).
Aldeyra Press Release—Aldeyra Therapeutics Presents Evidence for Aldehyde Sequestration as a Potential Therapeutic Approach in Succinic Semialdehyde Dehydrogenase Deficiency at the American Society of Human Genetics 2017 Annual Meeting, Oct. 24, 2017 (2 pages).
Aldeyra Press Release—Aldeyra Therapeutics Presents Noninfectious Anterior Uveitis Phase 2 Clinical Trial Data at the Association for Research in Vision and Ophthalmology 2017 Annual Meeting, May 17, 2017 (3 pages).
Aldeyra Press Release—Aldeyra Therapeutics Presents Noninfectious Anterior Uveitis Phase 2 Clinical Trial Data to the American Uveitis Society Held at the American Academy of Ophthalmology 2017 Annual Meeting, Nov. 29, 2017 (2 pages).
Aldeyra Press Release—Aldeyra Therapeutics Provides Update on Late-Stage Clinical Trials at 2016 Research and Development Day, Sep. 26, 2016 (2 pages).
Aldeyra Press Release—Aldeyra Therapeutics Provides Update on NS2 Clinical Program, Mar. 2, 2015 (2 pages).
Aldeyra Press Release—Aldeyra Therapeutics Provides Update on Ophthalmic Programs at 2019 Research & Development Day, Feb. 28, 2019 (2 pages).
Aldeyra Press Release—Aldeyra Therapeutics Schedules Conference Call and Webcast to Announce Results from Allergic Conjunctivitis Phase 2b Clinical Trial, Jun. 13, 2017 (1 page).
Aldeyra Press Release—Aldeyra Therapeutics Schedules Conference Call to Present Results of a Randomized, Double-Blind, Vehicle-Controlled Clinical Trial in Sjogren-Larsson Syndrome, Aug. 8, 2016 (2 pages).
Aldeyra Press Release—Aldeyra Therapeutics Schedules Webcast and Conference Call to Announce Results from Dry Eye Disease Phase 2a Clinical Trial, Sep. 11, 2017 (1 page).
Aldeyra Press Release—Aldeyra Therapeutics Selected for Podium Presentation of Phase 2a Dry Eye Disease Results at the 2018 Association for Research in Vision and Ophthalmology (ARVO) Annual Meeting, Feb. 21, 2018 (3 pages).
Aldeyra Press Release—Aldeyra Therapeutics Submits FDA IND Filing for Noninfectious Anterior Uveitis, Dec. 18, 2014 (2 pages).
Aldeyra Press Release—Aldeyra Therapeutics Submits IND Filing to FDA for Clinical Testing of NS2 in Patients With Sjogren-Larsson Syndrome, Jan. 5, 2015 (2 pages).
Aldeyra Press Release—Aldeyra Therapeutics to Host 2019 Research & Development Day, Feb. 12, 2019 (1 page).
Aldeyra Press Release—Aldeyra Therapeutics to Present at the 2016 SSADH Symposium, Mar. 24, 2016 (1 page).
Aldeyra Press Release—Aldeyra Therapeutics to Present Novel Data on a Potential Treatment for Sjogren-Larsson Syndrome at the 2015 Society for Inherited Metabolic Disorders Annual Meeting, Jan. 29, 2015 (2 pages).
Aldeyra Press Release—Aldeyra Therapeutics to Present Novel Data on a Potential Treatment for Succinic Semi-Aldehyde Dehydrogenase Deficiency at the 2015 American Society of Human Genetics (ASHG) Annual Meeting, Sep. 9, 2015 (2 pages).
Aldeyra Press Release—Aldeyra Therapeutics' Data on Lead Candidate NS2 to be Presented at Society for Investigative Dermatology 2014 Annual Meeting, May 8, 2014 (2 pages).
Aldeyra Press Release—Aldeyra Therapeutics, Inc. Announces Last Patient Dosed in Allergic Conjunctivitis Phase 2b Clinical Trial, Apr. 18, 2017 (2 pages).
Aldeyra Press Release—Aldeyra Therapeutics, Inc. Announces Last Patient Dosed in Phase II Clinical Trial of Topical Dermatologic NS2 in Patients With Sjögren-Larsson Syndrome Jun. 7, 2016 (2 pages).
Aldeyra Press Release—Aldeyra Therapeutics, Inc. Receives Orphan Drug Designation from the U.S. Food and Drug Administration for ADX-102 in Sjögren-Larsson Syndrome, Apr. 20, 2017 (2 pages).
Bacsi et al., "Effect of pollen-mediated oxidative stress on immediate hypersensitivity reactions and late-phase inflammation in allergic conjunctivitis," J. Allergy Clin. Immunol., 2005; 116(4):836-843.
Badii, "Allergic Conjunctivitis," https://www.healthline.com/health/allergic-conjunctivitis, Apr. 28, 2016 (12 pages) [retrieved on Nov. 22, 2019].
Boldogh et al., "ROS generated by pollen NADPH oxidase provide a signal that augments antigen-induced allergic airway inflammation," J. Clin. Invest., 2005; 115(8):2169-2179.
Ciolino et al., "Effect of alcaftadine 0.25% on ocular itch associated with seasonal or perennial allergic conjunctivitis: a pooled analysis of two multicenter randomized clinical trials," Clin Ophthalmol, 9:765-72 (May 2015).
ClinicalTrials.gov identifier NCT03162783, "A Randomized, Double Masked, Clinical Study of Subjects with Dry Eye Syndrome," (7 pages) (2017).
Davies, "Biopharmaceutical considerations in topical ocular drug delivery," Clin Exp Pharmacol Physiol, 27(7):558-62 (Jul. 2000).
Devillier et al., "The allergen challenge chamber: A valuable tool for optimizing the clinical development of pollen immunotherapy," Allergy, 2011; 66(2):163-9.
Ellis et al., "Multiple Doses of Trodusquemine Improve Glucose Tolerance in Type 2 Diabetic Subjects," 69th Scientific Sessions of the American Diabetes Association, Abstract No. 2071-PO (2009).
Goldstein et al., "A Phase 2 Exploratory Study of a Novel Interleukin-1 Receptor Inhibitor (EBI-005) in the Treatment of Moderate-to-Severe Allergic Conjunctivitis," Eye Contact Lens, 41(3):145-55 (May 2015).
Hessen et al., "Dry Eye: an Inflammatory Ocular Disease," J Ophthalmic Vis Res, 9(2):240-250 (2014).
Hom et al., "Allergic conjunctivitis and dry eye syndrome," Ann Allergy Asthma Immunol, 108(3):163-6 (Mar. 2012).
International Search Report and Written Opinion issued by the European Patent Office as International Searching Authority for International Patent Application No. PCT/US2019/044929 dated Nov. 20, 2019 (15 pages).
International Search Report and Written Opinion issued by the United States Patent and Trademark Office as International Searching Authority for International Patent Application No. PCT/US2019/041942 dated Sep. 30, 2019 (18 pages).

(56) References Cited

OTHER PUBLICATIONS

International Search Report and Written Opinion issued by the United States Patent and Trademark Office as International Searching Authority for International Patent Application No. PCT/US2019/045206 dated Oct. 17, 2019 (13 pages).
Jacobs et al., "Responses to ragweed pollen in a pollen challenge chamber versus seasonal exposure identify allergic rhinoconjunctivitis endotypes," J. Allergy Clin. Immunol., 2012; 130(1):122-7.
Leonardi, "Allergy and allergic mediators in tears," Exp. Eye Res., 2013; 117:106-17.
Liang et al., "Ocular safety of cationic emulsion of cyclosporine in an in vitro corneal wound-healing model and an acute in vivo rabbit model," Mol Vis, 18:2195-204 (2012).
Lopachin et al., "Molecular mechanisms of aldehyde toxicity: a chemical perspective," Chem Res Toxicol, 27(7):1081-91 (Jul. 2014).
Mathew et al., "Updates in the management of diabetic macular edema," J Diabetes Res. 2015; 2015:794036.
Mishra et al., "Recent Patents and Emerging Therapeutics in the Treatment of Allergic Conjunctivitis," Recent Pat. Inflamm. Allergy Drug Discov.; 2011; 5(1):26-36.
Nagai et al., Improved corneal toxicity and permeability of tranilast by the preparation of ophthalmic formulations containing its nanoparticles, J Oleo Sci, 63(2):177-86 (2014).
PCT International Search Report from PCT/US2019/054263 dated Jan. 6, 2020 (13 pages).
Pfaar et al., "Perspectives in allergen immunotherapy: 2017 and beyond," Allergy, 2018; 73(Suppl 104):5-23.
Pubchem, 1824609-67-7, SID 333824451, Apr. 24, 2017 (6 pages).
Rajewski et al., "Pharmaceutical applications of cyclodextrins. 2. In vivo drug delivery," J Pharm Sci, 85(11):1142-69 (Nov. 1996).
Restasis® Prescribing Information, Allergan, copyright 2016, revised 2017 (15 pages).
Rizzo et al., "Aldehyde Trapping Agent NS2 Blocks Formation of Fatty Aldehyde Adducts with Phosphatidylethanolamine and Suggests Potential Therapeutic Approach for Sjogren-Larsson Syndrome," Mol Genet and Metab, 114(3):362A (Mar. 2015) [Abstract Only].
Rizzo, Fatty aldehyde and fatty alcohol metabolism: review and importance for epidermal structure and function, Biochim Biophys Acta, 1841(3):377-89 (Mar. 2014).
Rønborg et al., "Exposure chamber for allergen challenge. The development and validation of a new concept," Allergy, 1996; 51(2):82-8.
Sanchez et al., "Allergic Conjunctivitis," J Investig Allergol Clin Immunol, 21(2):1-19 (2011).
Satici et al., "Malondialdehyde and antioxidant enzyme levels in the aqueous humor of rabbits in endotoxin-induced uveitis," EurJ Ophthalmol, 13(9-10):779-83 (Nov.-Dec. 2003).
Schaumberg et al., "Epidemiology of dry eye syndrome," Lacrimal Gland, Tear Film, and Dry Eye Syndromes 3, Kluwer Academic/Plenum Publishers, pp. 989-998 (2002).
Sheppard et al., Targeting Anterior Uveitis: A Focus on Iontophoresis and Other Advanced Technologies, Sep. 1, 2018 [Retrieved Nov. 11, 2019] Retrieved from Internet URL: https://www.nyee.edu/files/NYEE/Health%20Professionals/Continuing%20Medical%20Education/Enduring%20CME%20Activities/158 _ supplement.smaU_ v 1 _FINAL %20082818.pdf (8 pages).
Singh et al., "The epidemiology of ocular and nasal allergy in the United States, 1988-1994," J. Allergy Clin. Immunol., 2010; 126(4):778-783.
Spadea et al., "Corneal wound healing after laser vision correction," Br J Ophthalmol. 2016; 100:28-33.
Stevenson et al., "Dry eye disease: an immune-mediated ocular surface disorder," Arch Ophthalmol. 2012; 130(1): 90-100.
Tempest-Roe et al., "Local therapies for inflammatory eye disease in translation: past, present and future," BMC Ophthalmol, 13(1):39 (Aug. 2013).
U.S. Appl. No. 16/773,654, filed Jan. 27, 2020.
U.S. Appl. No. 16/825,898, filed Mar. 20, 2020.
Wakamatsu et al., "Evaluation of lipid oxidative stress status and inflammation in atopic ocular surface disease," Mol Vis, 16:2465-75 (Nov. 2010).
Weaver et al., "The Th17 pathway and inflammatory diseases of the intestines, lungs, and skin," Annu. Rev. Pathol., 8:477-512 (2013).
Webb et al., "Intralesional cytokines in chronic oxazolone-induced contact sensitivity suggest roles for tumor necrosis factor alpha and interleukin-4," J Invest Dermatol, 111(1):86-92 (Jul. 1998).
International Search Report and Written Opinion issued by the United States Patent and Trademark Office as International Searching Authority for International Patent Application No. PCT/US2020/031219, dated Aug. 31, 2020 (14 pages).
International Search Report and Written Opinion issued by the United States Patent and Trademark Office as International Searching Authority for International Patent Application No. PCT/US2019/052961, dated Dec. 10, 2019 (11 pages).
International Search Report and Written Opinion issued by the United States Patent and Trademark Office as International Searching Authority for International Patent Application No. PCT/US2019/054263, dated Jan. 6, 2020 (13 pages).
International Search Report and Written Opinion issued by the United States Patent and Trademark Office as International Searching Authority for International Patent Application No. PCT/US2019/064669, dated Feb. 27, 2020 (12 pages).
International Search Report and Written Opinion issued by the United States Patent and Trademark Office as International Searching Authority for International Patent Application No. PCT/US2020/024022, dated Jun. 17, 2020 (11 pages).
International Search Report and Written Opinion issued by the United States Patent and Trademark Office as International Searching Authority for International Patent Application No. PCT/US2020/031138, dated Jul. 13, 2020 (7 pages).

* cited by examiner

| | |
|---|---|
| Dosing | NS2 0.5% Topical Ocular<br>Pred Forte® 1% Topical Ocular |
| Randomization | Active-Controlled 1:1:1<br>NS2 QID, Pred Forte® QID Taper, NS2 QID + Pred Forte® BID Taper |
| Enrollment | 45 Patients with Active Disease |
| Treatment Time | 6 Weeks |
| Key Endpoints | Cell Count, Symptoms |

FIG. 1

NS2 Comparable to Corticosteroid in Non-Infectious Anterior Uveitis

|  | NS2 (n=15) | Pred Forte (n=13) | NS2 + Pred Forte (n=16) |
|---|---|---|---|
| Week 2 Cell Grade 0 | 5 (33%) | 4 (31%) | 5 (31%) |
| Week 8 Cell Grade 0 | 6 (40%) | 6 (46%) | 7 (44%) |
| ≥ 1 Cell Grade Reduction | 8 (53%) | 6 (46%) | 8 (50%) |
| Rescue Medication Required | 3 (20%) | 5 (38%) | 4 (25%) |

Notes:
- Grade 0 = One or zero cells in anterior chamber
- Patients were rescued at investigator discretion if no improvement or worsening of cell count.

*FIG. 2*

COMBINATION TREATMENT OF OCULAR INFLAMMATORY DISORDERS AND DISEASES

1. CROSS-REFERENCE TO RELATED APPLICATIONS

This application is a National Stage under 35 U.S.C § 371 of International application no. PCT/2017/031808, which claims the benefit under 35 U.S.C. § 119(e) of U.S. Provisional Application No. 62/333,549, filed May 9, 2016, the content of each of which is incorporated herein in their entirety by reference thereto.

2. BACKGROUND

Ocular inflammation can manifest in the form of numerous eye disorders of varying severity depending on the location of the inflammation. Disorders attributed to ocular inflammation include, among others, uveitis, allergic conjunctivitis, scleritis, optic neuritis, keratitis, and the like. Ocular inflammation has numerous causes ranging from autoimmune disorders, environment irritants, and injury such as surgery. Some forms of ocular inflammation occur secondary to bacterial or viral infection while some ocular inflammation have unknown etiology. Symptoms can include eye pain, eye redness, photophobia, floaters, loss of vision, or a combination of such symptoms.

Uveitis is typical of these ocular inflammatory disorders, and is characterized by inflammation of the uveal tract, which encompasses the iris, ciliary body, and choroid. Retinal inflammation is also classified as a type of uveitis. Uveitis can be anatomically classified as anterior (e.g., iritis and iridocyclitis), intermediate (e.g., cyclitis and peripheral uveitis), posterior (e.g., choroiditis and retinitis) and diffuse (e.g., iritis plus intermediate uveitis, chorioretinitis), also referred to as panuveitis. See Merck Manual Of Diagnosis And Therapy, 19th Ed., Elsevier Press (2011).

Repeated episodes of anterior uveitis can cause permanent and severe damage to the internal structures of the eye. Recurrent anterior uveitis can lead to the formation of considerable peripheral anterior synechia and secondary glaucoma. Chronic anterior uveitis can also cause corneal endothelial dysfunction and even cataract formation. Posterior inflammation can lead to persistent pathological vitreous alteration and retinal dysfunction, either of which may result in intractable visual loss.

During acute and chronic inflammation, various mediators of inflammation are released by the inflamed tissues and by leukocytes. The concentrations of these mediators and leukocytes are indicative of the level or degree of inflammation. Typical treatments for ocular inflammation target the inflammatory response. Anti-inflammatory steroidal preparations, for example, corticosteroids prednisolone and dexamethasone, are the drug of choice in the treatment of uveitis and other ocular inflammatory conditions. Other treatments for ocular inflammation involve immunomodulators, such as cyclosporin, tacrolimus, and sirolimus (i.e., rapamycin). However, use of steroids and other immunomodulators is complicated by severe and numerous side effects. Therefore, it would be highly desirable to develop effective alternative treatments that do not exhibit the undesirable immunomodulatory side effects but can also be used in combination with such standard immunomodulatory and other anti-inflammatory agents.

3. SUMMARY

The present disclosure provides a method of treating ocular inflammatory disorders and diseases by administering to a subject in need thereof a combination of a compound capable of reacting with aldehydes and an anti-inflammatory agent. In some embodiments, the compound has a structure of formula (I).

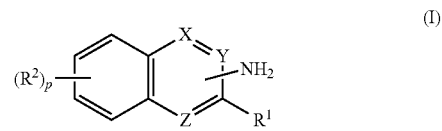

or a pharmaceutically acceptable salt thereof,
wherein,
X, Y and X are each independently N, CH or C with the $NH_2$ attached, wherein one of X, Y and Z is N;
$R^1$ is selected from the group consisting of

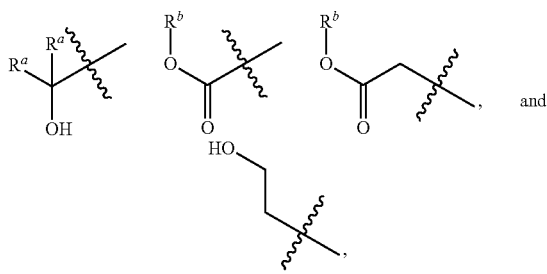

wherein,
$R^a$ is each independently a $C_{1-6}$ alkyl, and
$R^b$ is a substituted or unsubstituted $C_{1-6}$ alkyl;
$R^2$ is each independently a halogen, hydroxyl, carbamoyl, amino, or unsubstituted or substituted aryl; and
p is 0, 1, 2 or 3.

In some embodiments, the anti-inflammatory agent is selected from an anti-inflammatory steroid, non-steroidal anti-inflammatory compound, anti-metabolite, immunosuppressive antibiotic, alkylating agent, and an anti-inflammatory cytokine antibody.

In various embodiments, the ocular inflammatory disorder treatable with the combination therapy include allergic conjunctivitis, dry eye syndrome, meibomian gland dysfunction, cataracts, keratoconus, bullous and other keratopathy, Fuch's endothelial dystrophy, ocular cicatricial pemphigoid, conditions associated with photoreactive keratotomy (PRK) healing and other corneal healing, conditions associated with tear lipid degradation or lacrimal gland dysfunction, uveitis (e.g., anterior uveitis, intermediate uveitis, posterior uveitis, panuveitis, non-infectious uveitis, and infectious uveitis), keratitis, scleritis, iritis, cyclitis, ocular graft versus host disease (GVHD), optic neuritis, ocular Stevens Johnson Syndrome, blepharitis, ocular rosacea (with or without meibomian gland dysfunction), post cataract procedures, persistent corneal erosion, and inflammation associated with corneal trauma, corneal transplantation, and refractive surgery. In particular, the combination therapy is used to treat uveitis, such as anterior uveitis, intermediate uveitis, posterior uveitis, and panuveitis.

In some embodiments, the fused bicyclic amine compounds of formula (I) can be administered sequentially or concurrently with the anti-inflammatory agent, by the same or different route of administration. In some embodiments, the administration of the bicyclic amine compound is followed by administration of the anti-inflammatory agent. In some embodiments, the administration of the anti-inflammatory agent is followed by administration of the fused bicyclic amine compound.

In some embodiments, a therapeutically effective time interval is allowed between administration of the fused bicyclic amine compound and the anti-inflammatory agent, for example to avoid any adverse interactions and/or to maximize therapeutic effectiveness.

In some embodiments, the bicyclic amine compound and/or the anti-inflammatory agent is formulated for topical administration to the eye affected by the ocular inflammatory disorder or disease. In some embodiments, the bicyclic amine compound and/or the anti-inflammatory agent is formulated with an ophthalmically acceptable excipient. Exemplary ophthalmically acceptable excipients include, among others, one or more of a tonicity agent, preservative, buffering agent, wetting agent, viscosity enhancing agent, lubricating agent, chelating agent, and antioxidant.

In some embodiments, the bicyclic amine compound is formulated with a cyclodextrin, which in some embodiments, can be selected from α-cyclodextrin, β-cyclodextrin, γ-cyclodextrin, derivatives thereof, and combinations thereof. In particular, the cyclodextrin for use in the methods is selected from β-cyclodextrin, γ-cyclodextrin, derivatives thereof, and combinations thereof.

In some embodiments, the fused bicyclic amine compound can be present at a concentration of about 0.05% w/v to about 10% w/v, about 0.1% w/v to about 5% w/v, about 0.2% w/v to about 4% w/v, about 0.3% to about 3% w/v, about 0.4% w/v to about 2% w/v, or about 0.5% w/v to about 1.5% w/v. In some embodiments, the fused bicyclic amine compound can be present at a concentration of about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 1.5% w/v, about 2% w/v, about 3% w/v, about 4% w/v, about 5% w/v, about 6% w/v, about 7% w/v, about 8% w/v, about 9% w/v, or about 10% w/v.

In another aspect, further provided are kits comprising the fused bicyclic amine compound and the anti-inflammatory agent. In some embodiments, the kit can comprise single or multiple dosages of the bicyclic amine compound and the anti-inflammatory agent. The dosages, where appropriate can be in solid form, such as tablets and caplets, or in powder form, such as provided in capsules. In some embodiments, the dosages can be in liquid form, such as solutions for injection or topical administration, or provided as gels or creams for topical administration.

In some embodiments for topical administration, the kit comprises a solution of the bicyclic amine compound and the anti-inflammatory agent, either as a single pharmaceutical composition or as separate compositions, in single use vials, particularly single use plastic squeeze vials. The kit for topical administration can comprise a single dosage or multiple dosages.

4. BRIEF DESCRIPTION OF THE FIGURES

FIG. 1 shows the basic parameters of a clinical study examining the treatment of uveitis.

FIG. 2 shows the results of treatment with NS2 compound alone, and NS2 compound in combination with prednisolone acetate (Pred Forte®) on anterior chamber cell count, which is a marker for uveitis.

5. DETAILED DESCRIPTION

Figure 3:
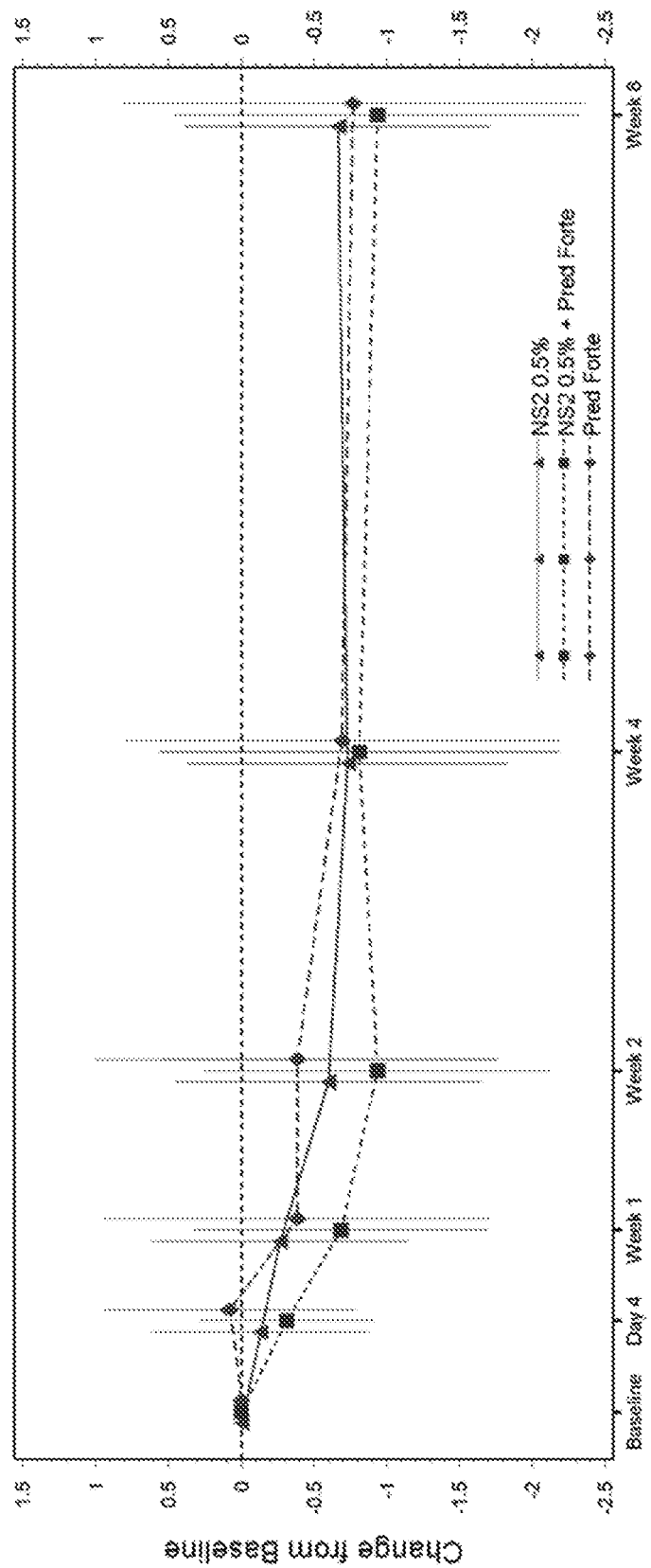
FIG. 3 is a graphical representation of the change in baseline of the anterior chamber cell count over the study period in the treatment groups (i.e., NS 0.5%; NS2 0.5%+Pred Forte®; and Pred Forte®).

The present disclosure provides a combination of a fused bicyclic amine compound and anti-inflammatory agent for treating ocular inflammatory disorders and diseases. Further provided are pharmaceutical compositions for treating ocular inflammatory disorders and diseases.

As used in this specification and the appended claims, the singular forms "a", "an" and "the" include plural referents unless the context clearly indicates otherwise. Thus, for example, reference to "a compound" includes more than one compound, and reference to "an excipient" includes more than one excipient.

It is further to be understood that use of "or" means "and/or" unless stated otherwise. Similarly, "comprise," "comprises," "comprising," "include," "includes," and "including" are interchangeable and not intended to be limiting. Also, where descriptions of various embodiments use the term "comprising," those skilled in the art would understand that in some specific instances, an embodiment can be alternatively described using language "consisting essentially of" or "consisting of."

The foregoing general description, including the drawings, and the following detailed description are exemplary and explanatory only and are not restrictive of this disclosure.

The section headings used herein are for organizational purposes only and not to be construed as limiting the subject matter described.

5.1. Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings:

"Combination therapy" or "therapeutically effective combination" refers to the administration of a first pharmaceutically active agent and at least a second pharmaceutically active agent, either simultaneously or separately, in any order to provide a therapeutically effective treatment of a disease or disorder.

"Alkyl" as used herein means a straight chain or branched non-cyclic hydrocarbon, preferably having 1 to 10 carbon atoms ($C_{1-10}$), more preferably having 1 to 6 carbon atoms ($C_{1-6}$).

"Aryl" used alone or as part of a larger moiety, such as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." Non-limiting examples of aryl groups include phenyl, naphthyl, and biphenyl.

"Halogen" refers to fluoro, chloro, bromo and iodo.

"Hydroxyl" refers to group —OH.

"Carbamoyl" refers to group —C(O)NH$_2$.

"Amino" refers to the group —NH$_2$. Substituted amino refers to the group —NHR', NR'R', and NR'R'R', where each R' is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Exemplary amino groups include, by way of example and not limitation, dimethylamino, diethylamino, trimethylammonium, triethylammonium, methylsulfonylamino, furanyl-oxy-sulfamino, and the like, as further described below.

"Substituted" whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned in the embodiments herein are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R°$; $-(CH_2)_{0-4}OR°$; $-O(CH_2)_{0-4}R°$, $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; $-CH=CHPh$, which may be substituted with $R°$; $-(CH_2)_{0-4}O(CH_2)_{0-1}$-pyridyl which may be substituted with $R°$; $-NO_2$; $-CN$; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-(CH_2)_{0-4}C(O)R°$; $-C(S)R°$; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; $-OC(O)(CH_2)_{0-4}SR-$, $SC(S)SR°$; $-(CH_2)_{0-4}SC(O)R°$; $-(CH_2)_{0-4}C(O)NR°_2$; $-C(S)NR°_2$; $-C(S)SR°$; $-SC(S)SR°$, $-(CH_2)_{0-4}OC(O)NR°_2$; $-C(O)N(OR°)R°$; $-C(O)C(O)R°$; $-C(O)CH_2C(O)R°$; $-C(NOR°)R°$; $-(CH_2)_{0-4}SSR°$; $-(CH_2)_{0-4}S(O)_2R°$; $-(CH_2)_{0-4}S(O)_2OR°$; $-(CH_2)_{0-4}OS(O)_2R°$; $-S(O)_2NR°_2$; $-(CH_2)_{0-4}S(O)R°$; $-N(R°)S(O)_2NR°_2$; $-N(R°)S(O)_2R°$; $-N(OR°)R°$; $-C(NH)NR°_2$; $-P(O)_2R°$; $-P(O)R°_2$; $-OP(O)R°_2$; $-OP(O)(OR°)_2$; $SiR°_3$; $-(C_{1-4}$ straight or branched alkylene)O$-N(R°)_2$; or $-(C_{1-4}$ straight or branched alkylene)C(O)O$-N(R°)_2$, wherein each $R°$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, $-(CH_2)_{0-2}R^•$, -(haloR$^•$), $-(CH_2)_{0-2}OH$, $-(CH_2)_{0-2}OR^•$, $-(CH_2)_{0-2}CH(OR^•)_2$; $-O(haloR^•)$, $-CN$, $-N_3$, $-(CH_2)_{0-2}C(O)R^•$, $-(CH_2)_{0-2}C(O)OH$, $-(CH_2)_{0-2}C(O)OR^•$, $-(CH_2)_{0-2}SR^•$, $-(CH_2)_{0-2}SH$, $-(CH_2)_{0-2}NH_2$, $-(CH_2)_{0-2}NHR^•$, $-(CH_2)_{0-2}NR^•_2$, $-NO_2$, $-SiR^•_3$, $-OSiR^•_3$, $-C(O)SR^•$, $-(C_{1-4}$ straight or branched alkylene)C(O)OR$^•$, or $-SSR^•$ wherein each $R^•$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^•$, -(haloR$^•$), $-OH$, $-OR^•$, $-O(haloR^•)$, $-CN$, $-C(O)OH$, $-C(O)OR^•$, $-NH_2$, $-NHR^•$, $-NR^•_2$, or $-NO_2$, wherein each $R^•$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^†$, $-NR^†_2$, $-C(O)R^†$, $-C(O)OR^†$, $-C(O)C(O)R^†$, $-C(O)CH_2C(O)R^†$, $-S(O)_2R^†$, $-S(O)_2NR^†_2$, $-C(S)NR^†_2$, $-C(NH)NR^†_2$, or $-N(R^†)S(O)_2R^†$; wherein each $R^†$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, $-R^•$, -(haloR$^•$), $-OH$, $-OR^•$, $-O(haloR^•)$, $-CN$, $-C(O)OH$, $-C(O)OR^•$, $-NH_2$, $-NHR^•$, $-NR^•_2$, or $-NO_2$, wherein each $R^•$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

"Pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge, S. M. et al., 1977, J Pharma Sci. 66:1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethane sulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

"Excipient" or "carrier" refers to any component of a pharmaceutical composition or formulation which, for example, serves as a bulking agent or acts as a stabilizing agent for the active ingredient or the composition.

"Therapeutically effective amount" refers to any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

"Treating" or "treatment" of a disease, disorder, or syndrome, as used herein, includes (i) preventing the disease, disorder, or syndrome from occurring in a subject, i.e. causing the clinical symptoms of the disease, disorder, or syndrome not to develop in an subject that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome.

"Prophylactic treatment" refers to a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder.

5.2. Combination Therapy of Ocular Inflammatory Disorders and Diseases

The present disclosure provides a combination of a fused bicyclic amine compound and an anti-inflammatory for use in treatment of ocular inflammatory disorders and diseases. Without being bound by any theory of operation, the fused bicyclic compound displays conjugate forming activity with toxic aldehydes. The compound is shown to be effective in treating an ocular inflammatory disorder, uveitis, either as monotherapy or in combination with an anti-inflammatory steroid.

Accordingly, the present disclosure provides a method of treating an ocular inflammatory disorder or disease, comprising administering to a subject with an ocular inflammatory disorder or disease a therapeutically effective amount of a compound of formula (I).

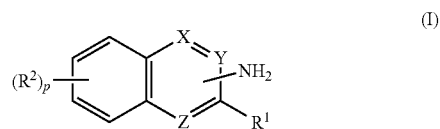

or a pharmaceutically acceptable salt thereof,
wherein,
X, Y and X are each independently N, CH or C with the $NH_2$ attached, wherein one of X, Y and Z is N;
$R^1$ is selected from the group consisting of

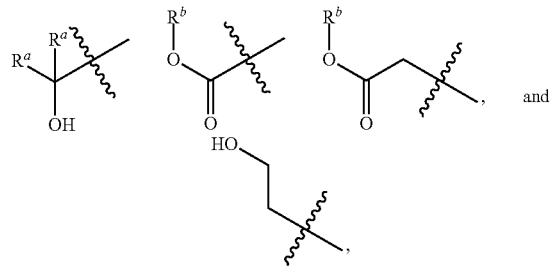

wherein,
$R^a$ is each independently a $C_{1-6}$ alkyl, and
$R^b$ is a substituted or unsubstituted $C_{1-6}$ alkyl; and
$R^2$ is each independently a halogen, hydroxyl, carbamoyl, amino, or unsubstituted or substituted aryl; and
p is 0, 1, 2 or 3; and
an anti-inflammatory agent.

In some embodiments, the compound of formula (I) is the compound of formula (1a):

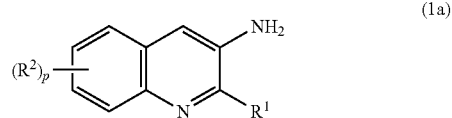

or a pharmaceutically acceptable salt thereof, wherein $R^1$, $R^2$ and p are defined as above.

In some embodiments, for the compound of formula (1a), $R^1$ is

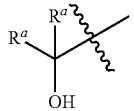

wherein,

R<sup>a</sup> is each independently a C$_{1-6}$ alkyl;

R$^2$ is each independently a halogen, hydroxyl, carbamoyl, amino, or unsubstituted or substituted aryl; and p is 0, 1, 2 or 3.

In some embodiments, each R$^a$ is independently a straight chain C$_{1-6}$ alkyl. In some embodiments, each R$^a$ is independently selected from the group consisting of methyl, ethyl, and propyl. In some embodiments, each R$^a$ is methyl.

In some embodiments, R$^2$ is a halogen, particularly Cl or F, and p is 1 or 2.

In some embodiments, the compound of formula (I) is Compound (2):

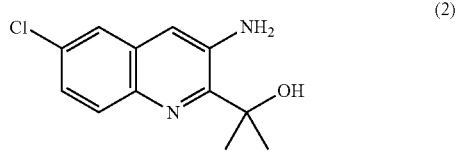 [SMILES: CC(C)(O)c1nc2ccc(Cl)cc2cc1N]

(2)

or a pharmaceutically acceptable salt thereof. Compound (2) is also referred to herein as NS2.

In the methods of treating ocular inflammatory disorders and diseases, the fused bicyclic amine compounds above are administered in combination with an anti-inflammatory agent. Anti-inflammatory agents useful for treating ocular inflammation in combination with the fused bicyclic amine compounds include, among others, a steroid, non-steroidal anti-inflammatory compound, anti-metabolite, immunosuppressive antibiotic, alkylating agent, and an anti-inflammatory cytokine antibody.

In some embodiments, the anti-inflammatory agent is a steroid, particularly a steroid with immunomodulatory, anti-inflammatory properties. In some embodiments, the anti-inflammatory is a glucocorticosteroid, which is widely used as effective treatments to control inflammatory and autoimmune diseases. In some embodiments, the glucocorticosteroid is a corticosteroid or a prodrug thereof. In some embodiments, the corticosteroid is selected from cortisol, cortisone, prednisone, prednisolone, methylprednisone, triamcinolone, betamethasone, dexamethasone and a prodrug thereof. In some embodiments, the corticosteroid prodrug is prednisolone acetate.

In some embodiments, the fused bicyclic amine compound is used in combination with a non-steroidal anti-inflammatory compound. These compounds generally act as inhibitors of the enzyme cyclooxygenase (COX), inhibiting the cyclooxygenase-1 (COX-1) and/or cyclooxygenase-2 (COX-2) isoenzymes. Different classes of non-steroidal anti-inflammatory compounds includes salicylates, propionic acid derivatives, acetic acid derivatives, enolic acid, anthranilic acid derivatives, and selective cox inhibitors. Exemplary non-steroidal anti-inflammatory compounds useful in the combination include, among others, acetylsalicylic acid, diflunisal, salsalate, ibuprofen, dexibuprofen, naioxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, phenylbutazone, mefenamic acid, meclofenamic acid, flufenamic acid, tolfenamic acid, and celecoxib. In some embodiments, for topical application to the eye, the non-steroidal anti-inflammatory compound can be selected from diclofenac, flurbiprofen, ketoprofen, bromfenac, and nepafenac.

In some embodiments, the anti-inflammatory agent for use in combination with the fused bicyclic amine compound is an anti-metabolite. In some embodiments, the anti-metabolite is a cytotoxic purine analog, for example, azathioprine and mercaptopurine. In some embodiments, the anti-metabolite is an anti-folate compound. Exemplary anti-folate compound is methotrexate. In some embodiments, the anti-metabolite is an inosine monophosphate dehydrogenase inhibitor (IMPDH), such as mycophenolic acid and its prodrug mycophenolate mofetil. In some embodiments, the anti-metabolite for use in the combination therapy is a dihydroorotate dehydrogenase inhibitor, such as leflunomide.

In some embodiments, the anti-inflammatory agent for use in combination with the fused bicyclic amine compound is an alkylating agent. Exemplary alkylating agents include, among others, cyclophosphamide and chlorambucil.

In some embodiments, the anti-inflammatory agent for use in combination with the fused bicyclic amine compound is an immunomodulatory antibiotic. Immunosuppressive antibiotics useful for the treatments herein include those that bind cyclophilin and/or calcineurin and inhibit T-lymphocyte activity. In some embodiments, the immunomodulatory antibiotic is selected from cyclosporine, tacrolimus, rapamycin, and derivatives thereof.

In some embodiments, the anti-inflammatory agent for use in the combination therapy is an anti-inflammatory antibody, such as an antibody targeting an inflammatory cytokine, such as TNFα, IL-1, IL-4, IL-5, or IL-17, or targeting an immune system cell active in the inflammatory response, such as B cells expressing CD20. In some embodiments, the anti-inflammatory biologic agent is selected from etanercept, infliximab, adalimumab, daclizumab, rituximab, toclizumab, certolizumab pegol, and golimumab.

The ocular inflammatory disorder treatable with the combination of the fused bicyclic amine compound and the anti-inflammatory agent include allergic conjunctivitis, including vernal keratoconjunctivitis and atopic keratoconjunctivitis; dry eye syndrome and meibomian gland dysfunction; cataracts; keratoconus; bullous and other keratopathy; Fuch's endothelial dystrophy; ocular cicatricial pemphigoid; conditions associated with photoreactive keratotomy (PRK) healing and other corneal healing; conditions associated with tear lipid degradation or lacrimal gland dysfunction; uveitis, including anterior uveitis, intermediate uveitis, posterior uveitis, panuveitis, non-infectious uveitis, and infectious uveitis; keratitis; scleritis; iritis; cyclitis; ocular graft versus host disease (GVHD); optic neuritis; ocular Stevens Johnson Syndrome; blepharitis; ocular rosacea, with or without meibomian gland dysfunction; post cataract; persistent corneal erosion; and inflammation associated with corneal trauma, corneal transplantation, and refractive surgery.

In some embodiments, the combination therapy is used to treat uveitis. In some embodiments, the uveitis treated with the combination is anterior uveitis, which includes the disorders of iridocyclitis and iritis and involves the anterior chamber and iris, with the latter indication also affecting the ciliary body. The vast majority of uveitis is anterior uveitis. In some embodiments, the uveitis treatable with the combination is intermediate uveitis, also referred to as pars planitis, which involves inflammation of cells in the vitreous cavity or deposition of inflammatory material on the pars plana. In some embodiments, the uveitis treatable with the combination is posterior uveitis, which involves inflammation of the uveal tract in the retina and the choroid. In some embodiments, the uveitis treatable with the combination is panuveitis (i.e., diffuse uveitis), which is inflammation of the uveal tract of both the anterior segment (e.g., iris and ciliary body) and the posterior segment (e.g., retina and choroid).

It is to be understood that while the description above are directed to combination treatment with the fused bicyclic amine compound and an anti-inflammatory agent, the data on treatment of uveitis indicates that the fused bicyclic amine compound has therapeutic efficacy when used alone, i.e., as monotherapy. Thus, for the each and every one of the ocular inflammatory disorders and diseases described in the present disclosure for treatment with the combination therapy, also provided are treatment with the fused bicyclic amine compounds, such as compound (2) without adjunctive administration of the anti-inflammatory agent, for example, as monotherapy.

In some embodiments, the combination of the fused bicyclic amine compound and the anti-inflammatory agent is used to treat macular degeneration. Accordingly, in some embodiments, a method of treating macular degeneration comprises administering to a subject in need thereof a therapeutically effective amount a fused bicyclic amine compound described herein, particularly compound (2), and an anti-inflammatory agent, as described herein. Thus, each and every combination of the fused bicyclic compound and the anti-inflammatory agent described for treatment of ocular inflammatory disorders and diseases can also be applied to treatment of macular degeneration. In some embodiments, the form of macular degeneration which can be treated is selected from age-related macular degeneration; Stargardt disease, an inherited form of juvenile macular degeneration; wet macular degeneration; dry macular degeneration; and geographic atrophy (GA) secondary to dry age related macular degeneration.

5.3. Pharmaceutical Compositions

In another aspect, the present disclosure provides pharmaceutical compositions for the treatment of ocular inflammatory disorders and diseases. In some embodiments, when the fused bicyclic amine compounds and the anti-inflammatory agent are administered separately, the compound and the anti-inflammatory agent can be prepared as separate pharmaceutical compositions. Separate pharmaceutical compositions of the compound and the anti-inflammatory agent are also used in concurrent administration, for example, if administered by different routes.

In some embodiments, the compound and the anti-inflammatory agent are prepared as an admixture for concurrent administration by the same route. In such a pharmaceutical composition, the compound and a compatible anti-inflammatory agent is formulated as a single pharmaceutical composition. The pharmaceutical composition can be prepared shortly before administration by mixing separate compositions of the compound and the anti-inflammatory agent. In some embodiments, the compound and the anti-inflammatory agent are provided as a stable composition and does not require mixing of the compound and the anti-inflammatory agent before use. Accordingly, in some embodiments, provided are a pharmaceutical composition of the fused bicyclic amine compound and an anti-inflammatory agent, as described above. In some embodiments, provided are a pharmaceutical composition of a compound of formula (I), particularly a compound of formula (1 a), and an anti-inflammatory agent. In some embodiments, the pharmaceutical composition comprises compound (2) and an anti-inflammatory agent.

In some embodiments, the pharmaceutical composition comprises the fused bicyclic amine compound and a steroid, as described above. In some embodiments, the steroid prepared as a pharmaceutical composition with the fused bicyclic amine compound is selected from cortisol, cortisone, prednisone, prednisolone, methylprednisone, triacmcinolone, betamethasone, dexamethasone, and prodrugs thereof. In some embodiments, the steroid prodrug is prednisolone acetate. In some embodiments, the pharmaceutical composition of the fused bicyclic amine compound and the steroid, such as prednisolone acetate, is formulated for topical ophthalmic administration.

In some embodiments, the pharmaceutical composition comprises the fused bicyclic amine compound and a non-steroidal anti-inflammatory agent, as described above. In some embodiments, the non-steroidal anti-inflammatory agent prepared as a pharmaceutical composition with the fused bicyclic amine compound is selected from acetylsalicylic acid, diflunisal, salsalate, ibuprofen, dexibuprofen, naioxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, phenylbutazone, mefenamic acid, meclofenamic acid, flufenamic acid, tolfenamic acid, and celecoxib. In a preferred embodiment, the bicyclic fused amine compound is formulated as a pharmaceutical composition with a non-steroidal anti-inflammatory agent selected from diclofenac, flurbiprofen, ketoprofen, bromfenac, and nepafenac, particularly for topical ophthalmic administration.

In some embodiments, the pharmaceutical composition comprises the fused bicyclic amine compound and an anti-metabolite. In some embodiments, the anti-metabolite prepared as a pharmaceutical composition with the fused bicyclic amine compound is selected from azathioprine, mercaptopurine, methotrexate, mycophenolic acid, mycophenolate mofetil and leflunomide. In some embodiments, the pharmaceutical composition of the fused bicyclic amine compound and the anti-metabolite is formulated for topical ophthalmic administration.

In some embodiments, the pharmaceutical composition comprises the fused bicyclic amine compound and an alkylating agent. In some embodiments, the alkylating agent prepared as a pharmaceutical composition with the fused bicyclic amine compound is selected from cyclophosphamide and chlorambucil. In some embodiments, the pharmaceutical composition of the fused bicyclic amine compound and the alkylating agent is formulated for topical ophthalmic administration.

In some embodiments, the pharmaceutical composition comprises the fused bicyclic amine compound and an immunomodulatory antibiotic. In some embodiments, the immunomodulatory antibiotic prepared as a pharmaceutical composition with the fused bicyclic amine compound is selected from cyclosporine, tacrolimus, rapamycin, and derivatives thereof. In some embodiments, the pharmaceutical composition of the fused bicyclic amine compound and the immunomodulatory antibiotic is formulated for topical ophthalmic administration.

The fused bicyclic amine compound and the anti-inflammatory agent, as described herein, whether separately or as an admixture, can be formulated in a conventional manner using one or more physiologically or pharmaceutically acceptable carriers or excipients. For example, fused bicyclic amine compounds and their pharmaceutically acceptable salts and solvates may be formulated for administration by, for example, injection, inhalation or insufflation (either through the mouth or the nose) or oral, buccal, sublingual, transdermal, nasal, ophthalmic, parenteral or rectal administration. In some embodiments, the bicyclic fused amine compound is administered to the eye for treatment of the ocular inflammatory disease or disorder.

The fused bicyclic amine compound and the anti-inflammatory agent can be formulated for a variety of modes of administration, including systemic, topical and localized administration. Techniques and formulations generally can be found in *Remington: The Science and Practice of Pharmacy*, 21$^{st}$ Ed., LWW (2005). For parenteral administration, the pharmaceutical compositions can be administered intramuscularly, intravenously, intraperitonealy, or subcutaneously. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

In some embodiments, the fused bicyclic amine compound and the anti-inflammatory agent, either separately or as an admixture, is formulated in a pharmaceutical composition with one or more pharmaceutically acceptable excipients or carriers.

For oral administration, the pharmaceutical compositions can take the form of, for example, tablets, lozenges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and/or sweetening agents as appropriate. Preparations for oral administration may be suitably formulated to give controlled release of the active compound.

For administration by inhalation (e.g., pulmonary delivery), the fused bicyclic amine compound and/or the anti-inflammatory agent can be conveniently delivered in the form of an aerosol spray ejected from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator can be formulated containing a powder mix of the compound and a suitable powder base such as lactose or starch.

In some embodiments, the fused bicyclic amine compound and/or the anti-inflammatory agent can be formulated for parenteral administration by injection, e.g., by bolus injection or continuous infusion. Formulations for injection may be presented in unit dosage form, e.g., in ampoules or in multi-dose containers, with or without an added preservative. The compositions may take such forms as suspensions, solutions or emulsions in oily or aqueous vehicles, and may contain excipients such as suspending, stabilizing and/or dispersing agents. Alternatively, the active ingredient may be in powder form for constitution with a suitable vehicle, e.g., sterile pyrogen-free water, before use.

In some embodiments, the fused bicyclic amine compound and/or the inflammatory agent can also be formulated as a depot preparation. Such long acting formulations can be administered by implantation (for example subcutaneously or intramuscularly) or by intramuscular injection. Thus, for example, pharmaceutically active compounds may be formulated with suitable polymeric or hydrophobic materials (for example as an emulsion in an acceptable oil) or ion exchange resins, or as sparingly soluble derivatives, for example, as a sparingly soluble salt. Controlled release formula also includes transdermal patches.

Liposomes are another drug delivery system which can be prepared, particularly as an injectable. Accordingly, in some embodiments, the pharmaceutically active agents can be administered in the form of a liposome delivery system. Liposomes are well-known in the art. Liposomes can be formed from a variety of phospholipids, such as phosphatidylcholine, cholesterol, and stearylamine. Various forms of liposomes suitable for the combination therapy encompass all types of liposomes, including, but not limited to, small unilamellar vesicles, large unilamellar vesicles and multilamellar vesicles.

In some embodiments, the fused bicyclic amine compounds and/or the anti-inflammatory agent can be prepared as rapidly disintegrating or dissolving dosage forms, which are useful for the rapid absorption, particularly buccal and sublingual absorption, of pharmaceutically active agents. Fast melt dosage forms are beneficial to patients, such as aged and pediatric patients, who have difficulty in swallowing typical solid dosage forms, such as caplets and tablets. Additionally, fast melt dosage forms circumvent drawbacks associated with, for example, chewable dosage forms, where the length of time an active agent remains in a patient's mouth plays an important role in determining the amount of taste masking and the extent to which a patient may object to throat grittiness of the active agent.

In some embodiments, a fused bicyclic amine compounds and/or the anti-inflammatory agent described herein, is incorporated into a topical formulation containing a topical carrier that is generally suited to topical drug administration and comprising any such material known in the art. The topical carrier can be selected so as to provide the composition in the desired form, e.g., as an ointment, lotion, cream, gel, oil, solution, or the like, and may be comprised of a material of either naturally occurring or synthetic origin. It is preferable that the selected carrier not adversely affect the active agents or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

In some embodiments, the fused bicyclic amine compounds and/or the anti-inflammatory agent can be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics, such as emolliency and the like. As with other carriers or vehicles, an ointment base should be inert, stable, nonirritating and nonsensitizing. In some embodiments, the ointments are formulated for ophthalmic applications, which can include viscous liquids or semisolid emulsions, either oil-in-water or water-in-oil. Ointments can contain an oil phase, an emulsifier and an aqueous phase. In some embodiments, the ointments can comprise petrolatum and/or a fatty alcohol such as cetyl or stearyl alcohol. The emulsifier can be generally a nonionic, anionic, cationic or amphoteric surfactant.

In some embodiments, the fused bicyclic amine compounds and/or the anti-inflammatory agent can be incorporated into gel formulations, which generally are semisolid systems consisting of either suspensions made up of small inorganic particles (two-phase systems) or large organic molecules distributed substantially uniformly throughout a carrier liquid (single phase gels). Although gels commonly employ an aqueous carrier liquid, alcohols and oils can be used as the carrier liquid as well.

In some embodiments, the pharmaceutical compositions comprise one or more preservatives to protect the pharmaceutical composition against antimicrobial (e.g., yeast, mold, bacteria) activity or stabilizes components in the composition. Preservatives include, but are not limited to, sodium benzoate, benzoic acid, ethylenediaminetetraacetic acid, sorbic acid, benzethonium chloride, benzalkonium chloride, bronopol, butyl paraben, methyl paraben, ethylparaben, propyl paraben, thiomerosol, sodium propionate, chlorhexidine, chlorobutanol, chlorocresol, cresol, imidurea, phenol, phenylmercuric salts, potassium sorbate, propylene glycol, and mixtures thereof. Generally, the total amount of preservative in the pharmaceutical compositions, such as solid formulations, solutions, ointments, etc., can be present from about 0.001 g/L to 0.10 g/L, such as 0.01 g per 100 ml of solution suspension or 100 g of formulation. As noted herein, in some embodiments, no preservatives are used.

In some embodiments, the fused bicyclic amine compounds and/or the anti-inflammatory agent, particularly when prepared as solution, such as for parenteral or topical ophthalmic administration, are prepared as an inclusion complex with cyclodextrin. In particular, for topical ophthalmic administration, the fused bicyclic amine compounds are formulated with a cyclodextrin, as described in U.S. patent publication no. 20120302601, incorporated herein by reference.

In some embodiments, the cyclodextrin for use in the pharmaceutical compositions can be selected from α-cyclodextrin, β-cyclodextrin, γ-cyclodextrin, derivatives thereof, and combinations thereof. In particular, the cyclodextrin for use in the methods is selected from β-cyclodextrin, γ-cyclodextrin, derivatives thereof, and combinations thereof.

In some embodiments, the cyclodextrin or derivative thereof is selected from carboxyalkyl cyclodextrin, hydroxyalkyl cyclodextrin, sulfoalkylether cyclodextrin, and an alkyl cyclodextrin. In various embodiments, the alkyl group in the cyclodextrin is methyl, ethyl, propyl, butyl, or pentyl.

In some embodiments, the cyclodextrin is α-cyclodextrin or a derivative thereof. In some embodiments, the α-cyclodextrin or derivative thereof is selected from carboxyalkyl-α-cyclodextrin, hydroxyalkyl-α-cyclodextrin, sulfoalkylether-α-cyclodextrin, alkyl-α-cyclodextrin, and combinations thereof. In some embodiments, the alkyl group in the α-cyclodextrin derivative is methyl, ethyl, propyl, butyl, or pentyl.

In some embodiments, the cyclodextrin is β-cyclodextrin or a derivative thereof. In some embodiments, the β-cyclodextrin or derivative thereof is selected from carboxyalkyl-β-cyclodextrin, hydroxyalkyl-β-cyclodextrin, sulfoalkylether-β-cyclodextrin, alkyl-β-cyclodextrin, and combinations thereof. In some embodiments, the alkyl group in the β-cyclodextrin derivative is methyl, ethyl, propyl, butyl, or pentyl.

In some embodiments, the β-cyclodextrin or a derivative thereof is hydroxyalkyl-β-cyclodextrin or sulfoalkylether-β-cyclodextrin. In some embodiments, the hydroxyalkyl-β-cyclodextrin is hydroxypropyl-β-cyclodextrin. In some embodiments, the sulfoalkylether-β-cyclodextrin is sulfobutylether-β-cyclodextrin. In some embodiments, β-cyclodextrin or a derivative thereof is alkyl-f-cyclodextrin, in particular methyl-β-cyclodextrin. In some embodiments using methyl-β-cyclodextrin, the β-cyclodextrin is randomly methylated β-cyclodextrin.

In some embodiments, the cyclodextrin is γ-cyclodextrin or a derivative thereof. In some embodiments, the γ-cyclodextrin or derivative thereof is selected from carboxyalkyl-γ-cyclodextrin, hydroxyalkyl-γ-cyclodextrin, sulfoalkylether-γ-cyclodextrin, and alkyl-γ-cyclodextrin. In some embodiments, the alkyl group in the γ-cyclodextrin derivative is methyl, ethyl, propyl, butyl, or pentyl. In some embodiments, the γ-cyclodextrin or derivative thereof is hydroxyalkyl-γ-cyclodextrin or sulfoalkylether-γ-cyclodextrin. In some embodiments, the hydroxyalkyl-γ-cyclodextrin is hydroxypropyl-γ-cyclodextrin.

When used in the formulation, the cyclodextrin can be present at about 0.1 w/v to about 30% w/v, about 0.1 w/v to about 20% w/v, about 0.5% w/v to about 10% w/v, or about 1% w/v to about 5% w/v. In some embodiments, the cyclodextrin is present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v or more.

In some embodiments, the fused bicyclic amine compound and the anti-inflammatory agent is, separately or as an admixture, formulated for ophthalmic administration. For ophthalmic topical administration, the dosage forms include solutions, ointments, gels (e.g., viscous or semi-viscous), emulsions, suspensions and solid eye drops and the like. In particular, aqueous solutions are generally preferred, based on ease of formulation and administration by a patient or medical professional. In some embodiment, the compositions are provided as lyophilized formulations, which can be reconstituted with an appropriate pharmaceutically acceptable solution.

In some embodiments, the ophthalmic compositions is formulated with one or more ophthalmic pharmaceutically acceptable additive or excipient. Accordingly, in some embodiments, an ophthalmic composition further comprises one or more of an ophthalmic pharmaceutically acceptable additive or excipient.

In some embodiments, the one or more ophthalmic pharmaceutically acceptable additive or excipient is selected from a tonicity agent, preservative, buffering agent, wetting agent, viscosity enhancing agent, lubricating agent, chelating agent, and antioxidant.

In some embodiments, the ophthalmic compositions can have one or more tonicity agents, which can be used to adjust the tonicity of the composition, for example, to the tonicity of natural tears. Suitable tonicity agents include, by way of example and not limitation, dextrans (e.g., dextran 40 or 70), dextrose, glycerin, potassium chloride, propylene glycol, and sodium chloride. Equivalent amounts of one or more salts made up of cations, for example, such as potassium, ammonium and anions such as chloride, citrate, ascorbate, borate, phosphate, bicarbonate, sulfate, thiosulfate, bisulfate, the salts sodium bisulfate and ammonium sulfate, can also be used. The amount of tonicity agent will vary, depending on the particular agent to be added. In general, however, the compositions can have a tonicity agent in an amount sufficient to cause the final composition to have an ophthalmically acceptable osmolarity. In some embodiments, the ophthalmic compositions have an osmolality of about 200 to about 1000 mOsm/L or about 200 to about 500 mOsm/L, or any specific value within said ranges (e.g., 200 mOsm/L, 210 mOsm/L, 220 mOsm/L, 230 mOsm/L, 240 mOsm/L, 250 mOsm/L, 260 mOsm/L, 270 mOsm/L, 280 mOsm/L, 290 mOsm/L, 300 mOsm/L, 310 mOsm/L, 320 mOsm/L, 330 mOsm/L, 340 mOsm/L, 350 mOsm/L, 360 mOsm/L, 370 mOsm/L, 380 mOsm/L, 390 mOsm/L or 400 mOsm/L). In a particular embodiment, the ophthalmic formulations are adjusted with a tonicity agent to an osmolality of ranging from about 250 to about 450 mOsm/L, or about 250 to about 350 mOsm/L.

In some embodiments, the ophthalmic composition can have one or more preservatives, for example, to extend shelf life or limit bacterial growth in the solutions during storage as well as when administered therapeutically onto the eye. Preservatives that can be used, include, among others, benzalkonium chloride, benzethonium chloride, benzododecinium bromide, cetylpyridinium chloride, chlorobutanol, ethylenediamine tetracetic acid (EDTA), thimerosal, phenylmercuric nitrate, phenylmercuric acetate, methyl/propylparabens, phenylethyl alcohol, sodium benzoate, sodium propionate, sorbic acid, and sodium perborate. The amount of preservative in the solution can be a level that enhances the shelf life, limits bacterial growth, or otherwise preserves the ocular solution, with minimal toxicity to the eye tissues (see, e.g., The United States Pharmacopeia, 22nd rev., and The National Formulary, 17th Ed. Rockville, Md.). Levels of preservative suitable for use in the ocular formulations can be determined by the person skilled in the art. In some embodiments, the preservatives can be used at an amount of from about 0.001 to about 1.0% w/v. For example, the preservative is present from about 0.005 to about 0.05% w/v, 0.005 to about 0.04% w/v, 0.01 to about 0.03% w/v, 0.01 to about 0.02% w/v, or from about 0.01 to about 0.015% w/v. In some embodiments, the amount of preservative can be about 0.005, 0.01, 0.012, 0.014, 0.016, 0.018, 0.02, 0.03, 0.04, or 0.05% w/v. In some embodiments, no preservatives are used in the ophthalmic compositions.

In some embodiments, the ophthalmic composition can have one or more buffering agents for adjusting and/or maintaining the pH of the ocular solution at a specified pH range. Generally, buffer capacity should be large enough to maintain the product pH for a reasonably long shelf-life but also low enough to allow rapid readjustment of the product to physiologic pH upon administration. Generally, buffer capacities of from about 0.01 to 0.1 can be used for ophthalmic solutions, particularly at concentrations that provide sufficient buffering capacity and minimizes adverse effects, e.g., irritation, to the eye. Exemplary buffering agents include, by way of example and not limitation, various salts (e.g., sodium, potassium, etc.), acids or bases, where appropriate, of the following agents, including among, others acetate, borate, phosphate, bicarbonate, carbonate, citrate, tetraborate, biphosphate, tromethamine, hydroxyethyl morpholine, and THAM (trishydroxymethyl-amino-methane). In some embodiments, the buffering agent can be present from about 0.5 mM to about 100 mM, from about 1 mM to about 50 mM, from about 1 mM to about 40 mM, from about 1 mM to about 30 mM, from about 1 mM to about 20 mM, or from about 1 mM to about 10 mM. In some embodiments, the buffering agent can be present at about 0.5 mM, about 1 mM, about 5 mM, about 10 mM, about 20 mM, about 30 mM, about 40 mM, about 50 mM, or about 100 mM.

In some embodiments, an exemplary buffering agent is phosphate, particularly sodium phosphate, which can be prepared by standard procedures, for example by mixing appropriate amounts of one or more monobasic phosphates, dibasic phosphates, and the like. In particular, useful phosphate buffers are prepared from phosphate salts of alkali and/or alkaline earth metals, such as sodium or potassium phosphate, including sodium monobasic phosphate, sodium dibasic phosphate, potassium monobasic phosphate, and potassium dibasic phosphate. In some embodiments, the phosphate buffering can be present from about 0.5 mM to about 100 mM, from about 1 mM to about 50 mM, from about 1 mM to about 40 mM, from about 1 mM to about 30 mM, from about 1 mM to about 20 mM, or from about 1 mM to about 10 mM. In some embodiments, the phosphate buffering agent can be present at about 0.5 mM, about 1 mM, about 5 mM, about 10 mM, about 20 mM, about 30 mM, about 40 mM, about 50 mM, or about 100 mM.

In some embodiments, the ophthalmic compositions can have one or more wetting agents. Generally, wetting agents can hydrate and limit drying of the eye. Wetting agents generally are hydrophilic polymers, including, by way of example and not limitation, polysorbate 20 and 80, poloxamer 282, and tyloxapol. In some embodiments, wetting agents also include, among others, cellulose based polymers, such as hydroxypropylmethylcellulose (HPMC) and carboxymethylcellulose (CMC); polyvinylpyrrolidone; and polyvinyl alcohol. In some embodiments, the concentration of wetting agent, such as HPMC, ranges from about 0.1% to about 2% w/v, about 0.5% to about 1% w/v, or any specific value within the ranges. In some embodiments, the concentration of wetting agent, such as HPMC, ranges from about 0.1% to about 1.0% w/v, or any specific value within said range (e.g., 0.1-0.2%, 0.2-0.3%, 0.3-0.4%, 0.4-0.5%, 0.5-0.6%, 0.6-0.7%, 0.7-0.8%, 0.8-0.9%, 0.9-1.0%; about 0.2%, about 0.21%, about 0.22%, about 0.23%, about 0.24%, about 0.25%, about 0.26%, about 0.27%, about 0.28%, about 0.29%, about 0.30%, about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

In some embodiments, the ophthalmic compositions can have one or more viscosity enhancing agents. The viscosity enhancing agent typically enhances the viscosity of the ocular solution to increase retention time of the solution on the eye, and in some instances, to provide a protective layer on the eye surface. Viscosity enhancing agents include, among others, carbopol gels, dextran 40 (molecular weight of 40,000 Daltons), dextran 70 (molecular weight of 70,000 Daltons), gelatin, glycerin, CMC, hydroxyethyl cellulose, HPMC, methylcellulose, ethylcellulose, polyethylene glycol, poloxamer 407, polysorbate 80, propylene glycol, polyvinyl alcohol, and polyvinylpyrrolidone (povidone), in various molecular weights and in various compatible combinations. In some embodiments, the ophthalmic compositions containing the pharmacology active agent(s) has a viscosity that ranges from about 10 to about 150 centipoise (cpi), about 15 to about 120 cpi, about 20 to about 90 cpi (or any specific value within said ranges). In some embodiments, the ophthalmic composition has a viscosity that ranges from about 15 cpi to about 30 cpi, or any specific value within the range (i.e., about 15 cpi, about 16 cpi, about 17 cpi, about 18 cpi, about 19 cpi, about 20 cpi, about 20 cpi, about 22 cpi, about 23 cpi, about 24 cpi, about 25 cpi, about 26 cpi, about 27 cpi, about 28 cpi, about 29 cpi, about 30 cpi). In some embodiments, the ophthalmic compositions containing the cyclodextrin has a viscosity that ranges from about 70 cpi to about 90 cpi, or any specific value within said range (i.e., about 70 cpi, about 71 cpi, about 72 cpi, about 73 cpi, about 74 cpi, about 75 cpi, about 76 cpi, about 77 cpi, about 78 cpi, about 79 cpi, about 80 cpi, about 81 cpi, about 82 cpi, about 83 cpi, about 84 cpi, about 85 cpi, about 86 cpi, about 87 cpi, about 88 cpi, about 89 cpi or about 90 cpi). In particular, the viscosity of from about 25 to about 50 cps are suitable for ophthalmic solutions.

In some embodiments, the ophthalmic compositions can have one or more lubricating agents. Ocular lubricants can approximate the consistency of endogenous tears and aid in natural tear build-up. Lubricating agents can include non-phospholipid and phospholipid-based agents. Ocular lubricants that are non-phospholipid based include, but are not limited to, propylene glycol; ethylene glycol; polyethylene glycol; hydroxypropylmethylcellulose; carboxymethylcellulose; hydroxypropylcellulose; dextrans, such as, dextran 70; water soluble proteins, such as gelatin; vinyl polymers, such as polyvinyl alcohol, polyvinylpyrrolidone, povidone; petrolatum; mineral oil; and carbomers, such as, carbomer 934P, carbomer 941, carbomer 940, and carbomer 974P. Non-phospholipid lubricants can also include compatible mixtures of any of the foregoing agents.

In some embodiments, the ophthalmic compositions can include one or more antioxidants. Suitable antioxidants, include, by way of example and not limitation, EDTA (e.g., disodium EDTA), sodium bisulphite, sodium metabisulphite, sodium thiosulfate, thiourea, and alpha-tocopherol.

In various embodiments, the pH of the ophthalmic composition can be within 1.0 to 1.5 pH units from physiological pH, particularly the physiological pH in the external environment of the eye. The pH of human tears is approximately pH 7.4. Hence, the pH of the ophthalmic solution can be about 1.0 to 1.5 pH units above or below pH 7.4. In some embodiments, the pH of the ophthalmic solution is from about pH 6.0 to about pH 8.5. In some embodiments, the pH of the ophthalmic solution is from about pH 6.0 to about pH 8.0. In some embodiments, the pH of the ophthalmic solution is from about 6.5 to about 8.0. In some embodiments, the pH of the ophthalmic solution is from about 7.0 to about 8.0. In some embodiments, the pH of the ophthalmic solution is from about 7.0 to about 7.5. In some embodiments, the pH of the ophthalmic is about 6.5, about 7, about 7.5, about 8, or about 8.5. A person of skill in the art can select a pH that balances the stability of the ophthalmic compositions and the tolerability of the eye to differences in pH from the natural condition. As is well known in the art, the pH of the solution can be adjusted by use of appropriate buffering agents and/or with an appropriate base (e.g., sodium hydroxide) or acid (e.g., hydrochloric acid).

5.4. Administration and Effective Dose

The fused bicyclic amine compounds and the anti-inflammatory agent can be administered to a subject with an ocular inflammatory disorder or disease by a variety of routes, either separately or concurrently. In some embodiments, the pharmaceutical compositions can be administered by injection, inhalation or insufflation (either through the mouth or the nose) or oral, buccal, sublingual, transdermal, nasal, ophthalmic, parenteral or rectal administration. For parenteral administration, the pharmaceutical compositions can be administered intramuscularly, intravenously, intraperitoneally, and subcutaneously.

In the methods of treating an ocular inflammatory disease or disorder, the fused bicyclic amine compounds and the anti-inflammatory agent are administered in a therapeutically effective amount to treat the subject with the ocular inflammatory disease or disorder. Generally, the subject to be treated with the combination therapy is a mammal, for example a dog, a cat, a horse, or a rabbit. In some embodiments, the subject is a non-human primate, for example a monkey, chimpanzee, or gorilla. In some embodiments, the subject is a human, sometimes referred to herein as a patient. In some embodiments, the human patient is an adult patient. In some embodiments, the human patient is a pediatric patient.

In the method of treating the ocular inflammatory disorder or disease, the fused bicyclic amine compound and the anti-inflammatory agent, or the pharmaceutical compositions thereof, can be administered sequentially or concurrently. In some embodiments, the fused bicyclic amine compound and the anti-inflammatory agent are administered concurrently by the same route. In some embodiments, the fused bicyclic amine compounds and the anti-inflammatory agent are administered concurrently by different routes. In some embodiments, the fused bicyclic amine compound and the anti-inflammatory agent are administered sequentially by the same route. In some embodiments, the fused bicyclic amine compound and the anti-inflammatory agent are administered sequentially by different routes. In some embodiments, the fused bicyclic amine compound is administered followed by administration of the anti-inflammatory agent. In some embodiments, the anti-inflammatory agent is administered followed by administration of the fused bicyclic amine compound. Where the fused bicyclic amine compound and the anti-inflammatory agents are administered at different times, in some embodiments, sufficient amount of time, or a therapeutically effective time interval, is allowed between administrations for avoiding any adverse interactions between the fused bicyclic amine compound and the anti-inflammatory agent and/or adverse interactions with excipients and/or carriers used in the respective pharmaceutical compositions, and also to maximize therapeutic effectiveness.

In the methods of treating an ocular inflammatory disorder or disease, the fused bicyclic amine compounds and the anti-inflammatory agent are administered in a therapeutically effective amount to treat the ocular inflammatory disease or disorder. In some embodiments, the dose is therapeutically effective in preventing the ocular inflammatory disorder or disease from occurring in a subject who previously had the disease or disorder; inhibiting the ocular inflammatory disease or disorder, or syndrome, i.e., arresting its development or progression of the ocular inflammatory disorder; or relieving the ocular inflammatory disease or disorder, such as causing regression of the ocular inflammatory disease or disorder, or reducing or eliminating associated symptoms of the ocular inflammatory disease or disorder.

In some embodiments, the fused bicyclic amine compounds and the anti-inflammatory agent are administered in an effective amount for prophylactic treatment to a subject who does not display signs or symptoms of an ocular inflammatory disease or disorder or displays only early signs or symptoms of the ocular disease or disorder, such that treatment is administered for the purpose of diminishing, preventing, or decreasing the risk of developing the disease, pathology, or medical disorder.

Determining a therapeutically effective dose can take into account, among others, whether the treatment is for an active disease or disorder or the use is for prophylactic treatment, the nature of the ocular inflammatory disorder, severity of the condition, the stage of the disease or disorder, the route of administration (e.g., systemic versus localized delivery), the subject, depending on the species, age, body weight, general health, sex, diet, time of administration, and drug interaction.

In some embodiments, for systemic administration, the fused bicyclic amine compounds can be administered orally or parenterally at dosage levels of about 0.01 mg/kg to about 50 mg/kg and preferably from about 1 mg/kg to about 25 mg/kg, of subject body weight per day, one or more times a day, weekly, biweekly or monthly to obtain the desired therapeutic effect.

For topical ophthalmic administration, the fused bicyclic amine compound can be present at a concentration of about 0.05% w/v to about 10% w/v, about 0.1% w/v to about 5% w/v, about 0.2% w/v to about 4% w/v, about 0.3% to about 3% w/v, about 0.4% w/v to about 2% w/v, or about 0.5% w/v to about 1.5% w/v. In some embodiments, the fused bicyclic amine compound can be present at a concentration at about least about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 1.5% w/v, about 2% w/v, about 3% w/v, about 4% w/v, about 5% w/v, about 6% w/v, about 7% w/v, about 8% w/v, about 9% w/v, or about 10% w/v. The amount administered topically can be about 20 to about 100 ul per dose, about 30 to 80 ul per dose or about 40 to 60 ul per dose. The volume can be estimated by the number of drops, where one drop is ~40-60 ul/drop (e.g., ~50 ul/drop) depending on the type of device used. Generally, a single drop is administered to the eye. In some embodiments, the compound is administered daily, weekly, biweekly or monthly. In some embodiments, the compound can be administered once per day, twice per day, three times per day, four times per day, five times per day, six times per day, seven times per day, eight times per day, or more as required to achieve a therapeutic effect. In some embodiments, the compound is administered topically once every 2 days or once every 3 days. In some embodiments, the compound is administered topically once a week, once every two weeks, or once a month.

The dose of the anti-inflammatory agent will take into account, in addition to the factors used in determining the therapeutically effective dose of the fused bicyclic amine compound, among others, the type of anti-inflammatory agent, the interactions of the fused bicyclic amine compound with the anti-inflammatory agent, such as the presence of synergy, and any adverse effects of the combination (e.g., toxicity). In some embodiments, standard dosages of the anti-inflammatory compounds can be used. Guidance is available in reference works, such as the Physician's Desk Reference, 70$^{th}$ Ed., PDR Network (2016), incorporated herein by reference, and in the prescribing information available for approved drugs.

Steroids can be administered systemically (e.g., orally) at 5 to 80 mg/day (e.g., 0.05 mg/kg to 1.5 mg/kg) once per day, two times per day, three times per day up to four times per day, depending on the results of the dosing. Initial treatment can be daily for 2 days or more, 3 days or more, 4 days or more, followed by a maintenance dose of about 0.5 to 1 mg/kg once per day, twice per day, three times per day, or 4 times per day.

For topical ophthalmic administration, the steroid can be present at a concentration of about 0.1 w/v to about 2% w/v, about 0.2 w/v to about 1.75% w/v, 0.5% w/v to about 1.5% w/v, 0.75% w/v to about 1.25% w/v. In some embodiments, the steroid is present at a concentration of about 0.1 w/v, 0.2% w/v, 0.5% w/v, 0.75% w/v, 1% w/v, 1.25% w/v, 1.5% w/v, about 1.75% w/v, or about 2% w/v. The ophthalmic steroid solution can be applied one once per day, twice per day, three times per day, four times per day, five times per day, six times per day, seven times per day, eight times per day, or more as required. For initial treatment, steroid can be applied once every two hours for the first two days and then 2 times per day, 3 times per day, or up to 4 times per day. An exemplary steroid for use as an adjunct to the fused bicyclic amine compounds is Pred Forte®, which is an ophthalmic formulation containing 1% prednisolone acetate, a prodrug form of prednisolone.

Non-steroidal anti-inflammatory compounds can be administered systemically (e.g., orally) at 0.1 mg/kg (e.g., 10 mg) to about 1.5 mg/kg (e.g., about 100 mg), depending on the specific type of non-steroidal anti-inflammatory compound, once per day, two times per day, three times per day, up to four times per day. For ophthalmic formulations, the non-steroidal anti-inflammatory compound can be present at 0.01% to about 0.5% w/v, depending on the specific type of drug. The ophthalmic formulation can be administered one time daily, two times daily, three times daily, up to four times daily. Specific prescribing information is available for oral and ophthalmic formulations for bromfenac, diclofenac, flurbiprofen, ketoprofen, and nepafenac. See Physician's Desk Reference, 70$^{th}$ Ed., PDR Network (2016), incorporated herein by reference.

Anti-metabolites are administered at dosages that depend on the specific type of agent. Methotrexate, for example, is prescribed for oral or intravenous administration at a dose of about 0.1 mg/kg (e.g., 7.5 mg) to about 0.4 mg/kg (e.g., 25 mg) once per week. Azathioprine is administered orally at dose of about 2 to 3 mg/kg/day and then adjusted based on clinical response. Mycophenolic acid and its prodrug mycophenolate mofetil can be prescribed at doses of about 500 mg/day to 1 g/day when administered systemically (e.g., oral). See, e.g., Baltatzis et al., 2003, Ophthalmology 110 (5):1061-1065. Ophthalmic formulation containing about 1% w/v to about 5% w/v of mycophenolic acid or mycophenolate mofetil can be administered once per day, twice per day, three times per day or up to four times per day. See, e.g., WO2006116591, incorporated herein by reference.

Immunomodulatory antibiotic cyclosporine can be administered systemically (e.g., orally) Cyclosporine can be administered at 2.5 mg/kg to about 5 mg/kg per day. Initial dose can use the lower dose and the dosage increased incrementally to the maximum dose. Tacrolimus can be administered systemically (e.g., orally) at a dose of 0.10 mg/kg to 0.15 mg/kg per day. Rapamycin can be administered systemically (e.g., orally) at a dose of about 2 to 6 mg/day. The initial dose can be at the higher dose followed by lower doses following initial treatment. Ophthalmic formulation of the immunomodulatory antibiotics can be prepared at concentrations of about 0.002% w/v to about 0.2% w/v, more preferably 0.02% w/v to about 0.1% w/v. See, e.g., U.S. Pat. No. 7,083,803. Ophthalmic formulation of 0.05% cyclosporine (0.5 mg/ml) is available under the name Restasis®. Ophthalmic formulation of the immunomodulatory antibiotic can be administered once per day up to twice per day or more as required to provide a therapeutic benefit in the combination therapy.

The cytotoxic effects of alkylating agents can limit their use. Cyclophosphamide is generally administered intravenously at a dose of about 1 g/cm$^2$. Treatments with cyclophosphamide can be given about once every two weeks. Chlorambucil can be administered orally at a dose of about 0.1 mg/kg to 0.2 mg/kg per day.

Where the anti-inflammatory agent is a biologic agent, the administration can be carried out according to the prescribing information. Etanercept can be administered subcutaneously, 25 mg twice a week. Infliximab can be administered intravenously at doses of about 3 mg/kg to about 5 mg/kg by infusions at weeks 0, 2, and 6. Maintenance therapy can be performed every 8 weeks following the initial therapy. Adalimumab (Humira®) is administered subcutaneously at a dose of 40 mg every two weeks. Daclizumab is administered intravenously at 1 mg/kg every 2 weeks, with an adjustment of the maximum dose to 200 mg per day.

The duration of treatment can be determined by the person of skill in the art, such as a physician or other medical personnel. In some embodiments, the treatment at an effective dosing regimen can be for up to 2 weeks, 4 weeks, 6 weeks, or 8 weeks or more. In some embodiments, the treatment can be up to 3 months, 4 months, 6 months, or up to 8 months. In some embodiments, the treatment can be for up to a year or more, or 2 years or more, or indefinitely as required to treat the ocular inflammatory disorder or disease. The person of skill in the art can determine the effective dosage, treatment regimen and duration of treatment for treating ocular inflammatory disorders with the combination treatment in view of the guidance provided in the present application.

In another aspect, the bicyclic amine compound and the anti-inflammatory agent can be provided in the form of a kit. In some embodiments, the kit comprises a bicyclic amine compound as described herein, and an anti-inflammatory agent. In some embodiments, the kit contains a single dosage or multiple dosages of the bicyclic amine compound and the anti-inflammatory agent. The bicyclic amine compound and/or the anti-inflammatory agent in the kit can be provided in solid or powder form, where appropriate, such as tablets or caplets or capsules. In some embodiments, the solid form can be provided in vials or blister packs, for example for a dosage sufficient for a defined period of treatment (e.g., day, week, month, etc.). In some embodiments, the bicyclic amine compound and/or the anti-inflammatory agent in the kit is in the form of gels or creams, such as for topical administration.

In some embodiments, the bicyclic amine compound and/or the anti-inflammatory agent of the kit can be provided as a solution, or in powder form for reconstitution with a suitable pharmaceutically acceptable solution, such as sterile water or saline. The solution can be provided in vials, tubes, ampoules, syringes, and the like. In some embodiments for topical ophthalmic administration, the bicyclic amine compound and/or the anti-inflammatory agent are provided in disposable vials, preferably single use vials, such as a plastic vial with snap off or tear off cap. The kit can also include measuring devices, such a droppers, graded cups or vials for measuring and/or dispensing the solutions.

6. EXAMPLES

Example 1: Randomized, Investigator-Masked Comparator Controlled Trial for Investigating NS2 Compound Eye Drops in Patients with Anterior Uveitis Uveitis is inflammation of the eye involving the uveal structures (e.g., iris, ciliary body and choroid). Anterior uveitis specifically refers to uveitis in the anterior segment of the eye. It can also involve the posterior segment of the eye or entire eye (panuveitis). Clinical signs and symptoms of anterior uveitis can include pain, blurry vision, conjunctival hyperemia, anterior chamber cells, anterior chamber flare, fibrin deposition and corneal endothelial inflammatory precipitates. Uveitis is not a single disease entity but rather a form of ocular inflammation associated with a diverse group of infectious and non-infectious conditions.

NS2 is a novel aldehyde-trapping agent formulated for this study as topical eye drops. Accumulation of toxic aldehyde metabolites such as malondialdehyde (MDA) is associated with anterior uveitis and other ocular and systemic diseases. There is evidence that prevention of toxic aldehyde formation and accumulation might prevent inflammation, fibrosis and oxidative damage associated with ocular disease (Sandikci et al., 2003, Acta Derm Venereol. 83(5):342-6; Cejkova et al., 2007 Histol Histopathol. 22(9): 997-1003; Balci et al., 2011, Mol Vis. 17:443-7; Turk et al., 2014, Ocul Immunol Inflamm. 22(2):127-32; Serbecic et al., 2005, Cell Tissue Res. 320(3):465-75; Demir et al., 2005, Ophthalmologica 219(1):49-53; Demir et al., 2010, Br J Ophthalmol. 94(8):1083-7). Furthermore, there is a need for safe and effective alternatives to corticosteroids as first line and adjunctive therapies for uveitis and other forms of ocular inflammation given the incidence of glaucoma, cataracts and corneal ulcers associated with chronic corticosteroid use. This study is designed to assess the safety and anti-inflammatory effect of NS2 eye drops in patients with non-infectious anterior uveitis as compared to an active comparator, Pred Forte® (prednisolone acetate ophthalmic suspension) 1%.

The proposed proof of concept study will use the 0.5% dose level of NS2. This dose was selected based on the Phase 1 clinical study results under IND 104,497 and a 9-month dog study with QID (OU) dosing at 0.5%, 0.25%, and 0.1% (w/v). In the clinical study, the 7 day QID dosing in the 0.5% NS2 group was well tolerated and plasma levels of NS2 remained below the detection limit (5 ng/ml) in each subject. NS2 was also well tolerated in the dog study and no abnormal findings were noted during macroscopic or microscopic evaluations. Based on the safety profile of the 9-month dog study where 0.5% NS2 was administered QID topically and the 7 day Phase 1 clinical study, a maximum treatment duration of 6-weeks was proposed.

To allow for continuous exposure, NS2 0.5% will be administered at a dose of 4 times per day in Group 1 and Group 2. Aldehydes at concentrations of 10 μM are cytotoxic in cell culture (Maeda et al., 2012, Nat Chem Biol. 8(2):170-8). Thus, in inflammatory disease, tissue concentrations of aldehydes are likely to be significantly lower. In primates, a single dose of 0.5% NS2 results in anterior eye tissue concentrations that range from 17.6 μM just after dosing to 1.2 μM three hours post dosing. These data suggest that, at the administration schedule in this study, tissue levels of NS2 should exceed tissue levels of aldehydes in uveitis subjects, possibly eliminating most, if not all, free aldehydes.

In summary, this study is a comparator-controlled clinical trial in which up to 45 subjects with non-infectious anterior uveitis will be randomized (1:1:1) to receive either:
Group 1—NS2 ophthalmic drops (0.5%);
Group 2—NS2 ophthalmic drops (0.5%) and Pred Forte® (prednisolone acetate ophthalmic suspension) 1%; or
Group 3—Pred Forte® (prednisolone acetate ophthalmic suspension) 1%.

The dosing schedule is summarized in Table 1.

TABLE I

Dosing Schedule for Eye Drop Regimens

| Week | Group I NS2 | Group I Pred | Group II NS2 | Group II Pred | Group III NS2 | Group III Pred |
|---|---|---|---|---|---|---|
| 1 | 4x/Day | None | 4x/Day | BID | None | QID |
| 2 | | | | BID | | TID |
| 3 | | | | Daily | | BID |
| 4 | | | | Daily | | BID |
| 5 | | | | None | | Daily |
| 6 | | | | None | | Daily |
| 7 | None | | None | None | | None |
| 8 | | | | | | |

Group 2 patients will alternate doses of NS2 and Pred Forte®. All patients will be instructed to maintain at least one hour between any two doses. Patients will be followed for up to 8 weeks and monitored for safety and efficacy at six scheduled visits. Efficacy will be assessed by standard ophthalmic examination procedures and response to treatment will be graded according to established uveitis scales.

Rescue therapy will be available to all patients that do not demonstrate a clinical response based on predefined rescue criteria. Rescue therapy will consist of therapy dosed at the clinical discretion of the treating physician. Rescued patients will receive a follow-up assessment one week after rescue, and then they will be discontinued from the study.

Each subject's study participation will consist of a Screening/Randomization Visit (Visit 1), Day 4 (Visit 2), Week 1 (Day 8+/−1 day; Visit 3), Week 2 (Day 15+/−1 day; Visit 4), Week 4 (Day 29+/−3 days; Visit 5) and Week 8 (Day 57+/−3 days; Visit 6/EoT). The total time of the study is approximately 8 weeks.

For each subject, a maximum of 6 scheduled visits and a Follow-up/EoS phone call one-week following the EOT/ET visit will be performed: The overall Schedule of Assessments for the study is provided in Table 2.

TABLE 2

Schedule of Visits and Assessments

| Test/Procedure | Day 1 | Day 4 | Week 1 | Week 2 | Week 4 | Week 8 (EOT/ET) | Week 9 (EOS)*** |
|---|---|---|---|---|---|---|---|
| Eligibility Criteria | ✓ | | | | | | |
| Informed Consent | ✓ | | | | | | |
| Medical History | ✓ | | | | | | |
| Uveitis Questionnaire | ✓ | | | | | | |
| Concomitant Medications | ✓ | ✓ | ✓ | ✓ | ✓ | ✓ | ✓ |
| Height, weight and vital signs | ✓ | | | | | | |
| Review Dosing Log | | ✓ | ✓ | ✓ | ✓ | ✓ | |
| Ocular pain, blurry vision, photophobia, tearing scores | ✓ | ✓ | ✓ | ✓ | ✓ | ✓ | |
| Laboratory tests and Chest X-Ray* | ✓ | | | | | | |
| Visual Acuity | ✓ | ✓ | ✓ | ✓ | ✓ | ✓ | |
| Slit lamp exam | ✓ | ✓ | ✓ | ✓ | ✓ | ✓ | |
| Intraocular pressure | ✓ | ✓ | ✓ | ✓ | ✓ | ✓ | |
| Funduscopy | ✓ | ✓ | ✓ | ✓ | ✓ | ✓ | |
| OCT | ✓ | | | | | ✓ | |
| Corneal pachymetry | ✓ | | | | | ✓ | |
| Adverse events | | ✓ | ✓ | ✓ | ✓ | ✓ | ✓ |
| Ocular photos** | ✓ | | | | | ✓ | |

*General labs (CBC with diff and CMP) will be drawn for all subjects as a baseline measurement. Uveitis-specific labs (HLA-B27, RPR, FTA-Abs, ACE, ANA) and Chest X-Ray will be obtained in patients experiencing their first episode of anterior uveitis only if their medical history is significant for risk factors for uveitis or in patients experiencing a repeat episode end prior tests of this nature have not been previously performed.
**Additional ocular photographs may be collected on Day 4 through Week 4 visits at the discretion of the investigator to document any clinically significant findings.
***The Week 9 End of Study visit will consist of a follow up phone call to collect final safety data.

Study drug will be self-administered by the patient (or caregiver). Subjects will be instructed to administer study drug per the treatment arm they are assigned to. Subjects randomized to NS2 or Pred Forte® will begin with one drop in the study eye four (4) times per day. Subjects randomized to the NS2 and Pred Forte® group will be instructed to administer one drop of NS2 four (4) times per day alternating with Pred Forte® two (2) times per day. Pred Forte® will be tapered weekly and continued for up to five (5) weeks as described in Table 1.

Evaluation of Study Protocol and Results. The Phase II clinical trial of topical ocular NS2 in patients with active noninfectious anterior uveitis shows that NS2 was statistically indistinguishable from standard of care corticosteroid administration in reducing inflammatory cell count in the anterior chamber of the eye. In a putative pro-inflammatory role, aldehydes appear to be upregulated early in inflammation and modify protein function via a novel signaling mechanism that involves binding certain amino acid residues. Sufficient aldehyde binding alters the function of proteins, particularly kinases and cellular receptors that then leads to activation of pro-inflammatory transcription factors, which in turn lead to an inflammatory response mediated by cytokines. Cytokines are classic targets of inflammation, but aldehydes have to date been ignored, and thus represent a novel target for the treatment of inflammatory disease.

The inflammatory pathway is affected by the balance of TH1 and TH2 cytokines, which are believed to cause the two common types of inflammation, autoimmune disease and allergy, respectively. In view of the positive data from Phase II clinical trial of topical ocular NS2 in allergic conjunctivitis, a common allergic disease affecting the eye, and the positive results on noninfectious anterior uveitis, NS2 has now demonstrated efficacy in autoimmune-like inflammation, and thus NS2, at least in the eye, represents a broad-based anti-inflammatory drug candidate with therapeutic application across many inflammatory diseases.

Data presented at the American Academy of Asthma, Allergy, and Immunology in 2015 indicated that, in a murine model of cytokine storm, systemically administered NS2 significantly lowered the levels of both TH1 (or auto-immune-related) and TH2 (or allergy-related) inflammatory cytokines while up-regulating IL-10, the most recognized anti-inflammatory cytokine. Data presented at the Association for Research in Vision and Ophthalmology (or ARVO) in 2015 indicated that, in a rat model of ocular inflammation, the activity of topical ocular NS2 compared favorably to that of topical ocular corticosteroid administration.

Based on the proposed role of aldehydes in mediating inflammation, in addition to the pre-clinical activity of NS2 in reducing IL-5 and other TH2 cytokines, a Phase II clinical trial of a single dose of topical ocular NS2 was initiated in patients with allergic conjunctivitis, and positive results were obtained from that trial in February 2016. The trial design and data from that trial have been reported previously. After a single eye drop, topical ocular NS2 significantly reduced ocular itching and tearing in allergic conjunctivitis. The positive clinical effects of NS2 continued after 14 days of dosing.

Based the pre-clinical activity of NS2 in diminishing TH1 cytokines as well as ocular inflammation in a pre-clinical model of uveitis, a Phase II trial of topical ocular NS2 was initiated in patients with active noninfectious anterior uveitis, a rare but serious autoimmune-like ocular disease that can lead to blindness. The design of the anterior uveitis Phase II trial was a randomized, parallel group, investigator-masked, comparator-controlled trial to evaluate the safety and efficacy of NS2 ophthalmic solution in patients with anterior uveitis. The trial assessed signs and symptoms of anterior uveitis including anterior chamber cell counts, which are utilized as the primary endpoints in registration studies of anterior uveitis. The study was conducted at 15 clinical sites in the US.

Forty five (45) subjects with non-infectious anterior uveitis were randomized to each of three treatment groups: two monotherapy groups and one combination treatment group. The groups were: NS2 ophthalmic drops 0.5% dosed four (4) times daily for 6 weeks; Pred Forte, that is, prednisolone acetate ophthalmic suspension 1%, dosed four (4) times daily and then tapered over the 6 weeks; and a combination treatment group in which NS2 ophthalmic drops 0.5% were dosed four (4) times daily for 6 weeks, which is the same regimen as the monotherapy group. Pred Forte® was dosed two (2) times daily and then tapered over a 4 week period. The randomization schedule resulted in 15 patients on NS2, 14 on Pred Forte® and 16 on the combination treatment. Prior to un-masking, one subject in the Pred Forte® group was removed from the ITT population for a history of ovarian cancer within the past 5 years, which met exclusion criteria. As a result analysis was performed on a modified intent-to-treat population with 13 patients in the Pred Forte® group.

Patients were followed for 8 weeks and monitored for safety and efficacy at six scheduled visits. Efficacy was assessed by standard ophthalmic examination procedures including slit lamp examination and response to treatment was graded according to established uveitis scales. The visit schedule included a screening randomization visit, a day 4 telephone follow-up visit, and clinic visits at week 1, 2, 4, and 8.

Rescue therapy, consisting of medication selected and dosed at the clinical discretion of the treating physician, was made available to all patients who did not demonstrate a clinical response based on standard predefined rescue criteria. Rescued patients were followed through the week 8 end of study visit.

As initially discussed above, the study results showed that NS2 produced clinically meaningful effects on anterior chamber cell counts, abbreviated as ACC, in this anterior uveitis population. This was seen both on the proportions of patients achieving the treatment response of grade 0 for ACC and also the proportions improving by at least 1 grade on ACC. These ACC treatment effects were comparable for the three treatment groups at most visits. At the week 2 study visit, grade 0 ACC treatment response was seen in 33% of NS2 patients, 31% of Pred Forte® patients and 31% of combination patients. At the week 8 study visit, sustained grade 0 ACC treatment response was seen in 40% of NS2 patients, 46% of Pred Forte® patients, and 44% of combination patients. For ACC improvement of at least 1 grade, a successful response was seen in 53% of NS2 patients, 46% of Pred Forte® patients, and 50% of combination patients. Rescue medication rates during the study were also similar between NS2 and Pred Forte®, with rescue medication required in 20% of NS2 patients, 38% of Pred Forte patients, and 25% of combination patients.

For both the last observation carried forward (LOCF) and non-LOCF mITT populations, the pattern of reduction in ACC was comparable among the three treatment groups. It is worth noting that the responses on anterior chamber flare were similar to the effects described for anterior chamber cell counts.

Although the trial size is small and not formally powered, there were no statistically significant differences evidenced between the three treatment groups on any of these objective ophthalmic examination endpoints.

NS2 was generally well tolerated in the anterior uveitis population and there were no safety concerns during the study, including ocular exam scores, intra-ocular pressure, corneal thickness and visual acuity. There was an increased frequency of ocular stinging and burning in the NS2 treated groups. These types of adverse events are not uncommon with current topical ocular therapies. One subject in the NS2 group and one subject in combination group withdrew for an adverse event of stinging. There were no serious adverse events.

The outcome has been described as a very encouraging clinical trial with NS2 demonstrating clear activity in anterior uveitis with no evidence of significant adverse effects. This suggests that NS2 may be an important future treatment option for anterior uveitis patients. Effectiveness equal to topical corticosteroids with the absence of eye pressure elevation properties or cataract production would make this anti-inflammatory therapy an attractive therapeutic option for treating uveitis.

In addition, based on the successful demonstration of clinically meaningful activity in two out of two ocular studies and with the encouragement from clinical ophthalmology experts, additional ocular inflammation Phase II trial designs at present, both in rare and common diseases, are being evaluated.

While it is clear that noninfectious anterior uveitis and other ocular diseases are often treated with topical corticosteroids, corticosteroids often lead to cataracts, glaucoma, and other ocular complications that result in significant and costly morbidity. Thus, in ocular inflammation, as well as in inflammation that affects other aspects of the body, there is a considerable need for novel non-steroidal therapies. Given that NS2 has demonstrated activity in the two major forms of ocular inflammation, there are other potential indications for NS2 were NS2 to successfully complete clinical development and receive marketing approval from regulatory agencies. There are many diseases where NS2 may have clinical utility, and in aggregate those diseases represent many patients. For example, it is estimated that there are approximately 1 million allergic conjunctivitis patients that are resistant to anti-histamines, the mainstay of therapy in that disease, and require topical corticosteroids for effective symptomatic control. Branded corticosteroid therapy, on average, may cost as much as $400 per course. Based on 2015 IMS data, topical ocular corticosteroids represented approximately $1.5B in revenues, about 80% of which is derived from branded products. Thus, the current market for novel non-steroidal anti-inflammatory medication for the treatment of ocular inflammation is substantial.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

We claim:

1. A method of treating non-infectious anterior uveitis, comprising administering to a subject with non-infectious anterior uveitis a therapeutically effective amount of Compound (2):

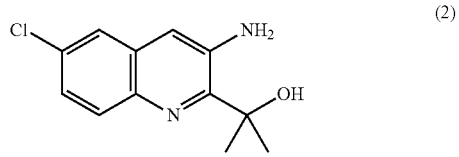 [SMILES: CC(C)(O)c1nc2ccc(Cl)cc2cc1N]

or a pharmaceutically acceptable salt thereof; and prednisolone.

2. The method of claim 1, wherein Compound (2) is formulated with a β-cyclodextrin or derivatives thereof.

3. The method of claim 2, wherein the β-cyclodextrin or derivatives thereof is sulfobutylether-β-cyclodextrin or hydroxypropyl-β-cyclodextrin.

4. The method of claim 1, wherein Compound (2) is administered topically at a concentration of about 0.1% w/v to about 5% w/v.

* * * * *